US008963726B2

(12) United States Patent
Kates

(10) Patent No.: US 8,963,726 B2
(45) Date of Patent: Feb. 24, 2015

(54) SYSTEM AND METHOD FOR HIGH-SENSITIVITY SENSOR

(71) Applicant: Nest Labs, Inc., Palo Alto, CA (US)

(72) Inventor: Lawrence Kates, Corona Del Mar, CA (US)

(73) Assignee: Google Inc., Mountain View, CA (US)

( * ) Notice: Subject to any disclaimer, the term of this patent is extended or adjusted under 35 U.S.C. 154(b) by 0 days.

(21) Appl. No.: 14/165,003

(22) Filed: Jan. 27, 2014

(65) Prior Publication Data

US 2014/0203935 A1    Jul. 24, 2014

Related U.S. Application Data

(63) Continuation of application No. 12/624,838, filed on Nov. 24, 2009, now Pat. No. 8,638,215, which is a continuation of application No. 11/494,988, filed on Jul. 28, 2006, now Pat. No. 7,623,028, which is a continuation-in-part of application No. 10/856,390, filed on May 27, 2004, now Pat. No. 7,102,505.

(51) Int. Cl.
*G08B 17/10* (2006.01)
*G08B 21/18* (2006.01)
*G01N 33/00* (2006.01)
(Continued)

(52) U.S. Cl.
CPC .......... *G08B 21/182* (2013.01); *G01N 33/0065* (2013.01); *G08B 1/08* (2013.01); *G08B 25/009* (2013.01); *G08B 29/26* (2013.01); *G08B 17/10* (2013.01); *G08B 25/10* (2013.01)
USPC ............................ 340/628; 340/627; 340/577

(58) Field of Classification Search
CPC combination set(s) only.
See application file for complete search history.

(56) References Cited

U.S. PATENT DOCUMENTS 2,233,297 A    2/1941    Polin et al.
3,991,357 A    11/1976    Kaminski
(Continued)

FOREIGN PATENT DOCUMENTS

CA    2202008    2/2000
CN    2388660    7/2000
(Continued)

OTHER PUBLICATIONS

Aprilaire Electronic Thermostats Model 8355 User's Manual, Research Products Corporation, Dec. 2000, 16 pages.
(Continued)

*Primary Examiner* — Travis Hunnings
(74) *Attorney, Agent, or Firm* — Kilpatrick Townsend & Stockton LLP

(57) ABSTRACT

A sensor unit that includes at least one sensor configured to measure an ambient condition is described. The controller can be configured to receive instructions, to report a notice level when the controller determines that data measured by the at least one sensor fails a report threshold test corresponding to a report threshold value. The controller can also be configured to obtain a plurality of calibration measurements from the at least one sensor during a calibration period and to adjust the threshold based on the calibration measurements. The controller can be configured to compute a first threshold level corresponding to background noise and a second threshold level corresponding to sensor noise, and to compute the report threshold value from the second threshold. In one embodiment, the sensor unit adjusts one or more of the thresholds based on ambient temperature.

20 Claims, 12 Drawing Sheets

(51) Int. Cl.
  *G08B 1/08* (2006.01)
  *G08B 25/00* (2006.01)
  *G08B 29/26* (2006.01)
  *G08B 25/10* (2006.01)

(56) References Cited

U.S. PATENT DOCUMENTS

| | | | |
|---|---|---|---|
| 4,061,442 A | 12/1977 | Clark et al. | |
| 4,099,168 A | 7/1978 | Kedjierski et al. | |
| 4,136,823 A | 1/1979 | Kullberg | |
| 4,183,290 A | 1/1980 | Kucharczyk | |
| 4,223,831 A | 9/1980 | Szarka | |
| 4,226,533 A | 10/1980 | Snowman | |
| 4,266,218 A * | 5/1981 | Kardash | 340/628 |
| 4,266,220 A | 5/1981 | Malinowski | |
| 4,335,847 A | 6/1982 | Levine | |
| 4,400,694 A | 8/1983 | Wong et al. | |
| 4,408,711 A | 10/1983 | Levine | |
| 4,420,746 A | 12/1983 | Malinowski | |
| 4,437,336 A | 3/1984 | Abe | |
| 4,455,553 A | 6/1984 | Johnson | |
| 4,514,720 A | 4/1985 | Oberstein et al. | |
| 4,535,450 A | 8/1985 | Tan | |
| 4,539,556 A * | 9/1985 | Dederich et al. | 340/515 |
| 4,543,570 A | 9/1985 | Bressert et al. | |
| 4,556,873 A | 12/1985 | Yamada et al. | |
| 4,615,380 A | 10/1986 | Beckey | |
| 4,652,859 A | 3/1987 | Van Wienen | |
| 4,661,804 A | 4/1987 | Abel | |
| 4,670,739 A | 6/1987 | Kelly, Jr. | |
| 4,674,027 A | 6/1987 | Beckey | |
| 4,675,661 A | 6/1987 | Ishii | |
| 4,685,614 A | 8/1987 | Levine | |
| 4,688,183 A * | 8/1987 | Carll et al. | 700/275 |
| 4,692,742 A | 9/1987 | Raizen et al. | |
| 4,692,750 A | 9/1987 | Murakami et al. | |
| 4,727,359 A | 2/1988 | Yuchi et al. | |
| 4,751,961 A | 6/1988 | Levine et al. | |
| 4,772,876 A | 9/1988 | Laud | |
| 4,801,865 A | 1/1989 | Miller et al. | |
| 4,811,011 A | 3/1989 | Sollinger | |
| 4,817,131 A | 3/1989 | Thornborough et al. | |
| 4,827,244 A | 5/1989 | Bellavia et al. | |
| 4,862,514 A | 8/1989 | Kedjierski | |
| 4,871,999 A | 10/1989 | Ishii et al. | |
| 4,897,798 A | 1/1990 | Cler | |
| 4,901,316 A | 2/1990 | Igarashi et al. | |
| 4,916,432 A | 4/1990 | Tice et al. | |
| 4,939,504 A | 7/1990 | Miller | |
| 4,951,029 A | 8/1990 | Severson | |
| 4,971,136 A | 11/1990 | Mathur et al. | |
| 4,977,527 A | 12/1990 | Shaw et al. | |
| 4,996,518 A | 2/1991 | Takahashi et al. | |
| 5,088,645 A | 2/1992 | Bell | |
| 5,107,446 A | 4/1992 | Shaw et al. | |
| 5,134,644 A | 7/1992 | Garton et al. | |
| 5,138,562 A | 8/1992 | Shaw et al. | |
| 5,151,683 A | 9/1992 | Takahashi et al. | |
| 5,159,315 A | 10/1992 | Schultz et al. | |
| 5,168,262 A | 12/1992 | Okayama | |
| 5,188,143 A | 2/1993 | Krebs | |
| 5,211,332 A | 5/1993 | Adams | |
| 5,229,750 A | 7/1993 | Welch et al. | |
| 5,240,022 A | 8/1993 | Franklin | |
| 5,240,178 A | 8/1993 | Dewolf et al. | |
| 5,244,146 A | 9/1993 | Jefferson et al. | |
| 5,254,035 A | 10/1993 | Kiuchi | |
| 5,260,687 A | 11/1993 | Yamauchi et al. | |
| 5,267,180 A | 11/1993 | Okayama | |
| 5,281,951 A | 1/1994 | Okayama | |
| 5,315,291 A | 5/1994 | Furr | |
| 5,319,698 A | 6/1994 | Glidewell et al. | |
| 5,335,186 A | 8/1994 | Tarrant | |
| 5,345,224 A | 9/1994 | Brown | |
| 5,357,241 A | 10/1994 | Welch, Jr. | |
| 5,395,042 A | 3/1995 | Riley et al. | |
| 5,400,246 A | 3/1995 | Wilson et al. | |
| 5,408,223 A | 4/1995 | Guillemot | |
| 5,430,433 A | 7/1995 | Shima | |
| 5,432,500 A | 7/1995 | Scripps | |
| 5,476,221 A | 12/1995 | Seymour | |
| 5,499,196 A | 3/1996 | Pacheco | |
| 5,530,433 A | 6/1996 | Morita | |
| 5,555,927 A | 9/1996 | Shah | |
| 5,568,121 A | 10/1996 | Lamensdorf | |
| 5,574,435 A | 11/1996 | Mochizuki | |
| 5,611,484 A | 3/1997 | Uhrich | |
| 5,627,515 A | 5/1997 | Anderson | |
| 5,655,561 A | 8/1997 | Wendel et al. | |
| 5,719,556 A | 2/1998 | Albin et al. | |
| 5,736,928 A | 4/1998 | Tice et al. | |
| 5,748,092 A | 5/1998 | Arsenault et al. | |
| 5,808,294 A | 9/1998 | Neumann | |
| 5,854,994 A | 12/1998 | Canada et al. | |
| 5,859,536 A | 1/1999 | Stockton | |
| 5,881,951 A | 3/1999 | Carpenter | |
| 5,889,468 A | 3/1999 | Banga | |
| 5,892,758 A | 4/1999 | Argyroudis | |
| 5,898,374 A | 4/1999 | Schepka | |
| 5,902,183 A | 5/1999 | D'Souza | |
| 5,907,491 A | 5/1999 | Canada et al. | |
| 5,909,378 A | 6/1999 | De Milleville | |
| 5,918,474 A | 7/1999 | Khanpara et al. | |
| 5,923,102 A | 7/1999 | Koenig et al. | |
| 5,949,332 A | 9/1999 | Kim | |
| 5,959,529 A | 9/1999 | Kail, IV | |
| 5,977,964 A | 11/1999 | Williams et al. | |
| 6,025,788 A | 2/2000 | Diduck | |
| 6,031,455 A | 2/2000 | Grube et al. | |
| 6,049,273 A | 4/2000 | Hess | |
| 6,060,994 A | 5/2000 | Chen | |
| 6,062,482 A | 5/2000 | Gauthier et al. | |
| 6,072,784 A | 6/2000 | Agrawal et al. | |
| 6,075,451 A | 6/2000 | Lebowitz et al. | |
| 6,078,050 A | 6/2000 | Castleman | |
| 6,078,269 A | 6/2000 | Markwell et al. | |
| 6,084,522 A | 7/2000 | Addy | |
| 6,088,688 A | 7/2000 | Crooks et al. | |
| 6,095,427 A | 8/2000 | Hoium et al. | |
| 6,097,288 A | 8/2000 | Koeppe, Jr. | |
| 6,098,893 A | 8/2000 | Berglund et al. | |
| 6,110,038 A | 8/2000 | Stern | |
| 6,157,307 A | 12/2000 | Hardin | |
| 6,175,310 B1 | 1/2001 | Gott | |
| 6,208,247 B1 | 3/2001 | Agre et al. | |
| 6,215,404 B1 | 4/2001 | Morales | |
| 6,216,956 B1 | 4/2001 | Ehlers et al. | |
| 6,222,448 B1 | 4/2001 | Beck et al. | |
| 6,222,456 B1 * | 4/2001 | Tice | 340/630 |
| 6,313,646 B1 | 11/2001 | Davis et al. | |
| 6,320,501 B1 | 11/2001 | Tice et al. | |
| 6,349,883 B1 | 2/2002 | Simmons et al. | |
| 6,356,204 B1 | 3/2002 | Guindi et al. | |
| 6,369,714 B2 | 4/2002 | Walter | |
| 6,370,894 B1 | 4/2002 | Thompson et al. | |
| 6,377,181 B1 | 4/2002 | Kroll et al. | |
| 6,380,860 B1 | 4/2002 | Goetz | |
| 6,388,399 B1 | 5/2002 | Eckel et al. | |
| 6,415,205 B1 | 7/2002 | Myron et al. | |
| 6,420,973 B2 | 7/2002 | Acevedo | |
| 6,437,692 B1 | 8/2002 | Petite et al. | |
| 6,441,731 B1 | 8/2002 | Hess | |
| 6,445,292 B1 | 9/2002 | Jen et al. | |
| 6,453,687 B2 | 9/2002 | Sharood et al. | |
| 6,478,233 B1 | 11/2002 | Shah | |
| 6,489,895 B1 | 12/2002 | Apelman | |
| 6,515,283 B1 | 2/2003 | Castleman et al. | |
| 6,526,807 B1 | 3/2003 | Doumit et al. | |
| 6,535,110 B1 | 3/2003 | Arora et al. | |
| 6,552,647 B1 | 4/2003 | Thiessen et al. | |
| 6,553,336 B1 | 4/2003 | Johnson et al. | |
| 6,583,720 B1 | 6/2003 | Quigley | |
| 6,615,658 B2 | 9/2003 | Snelling | |
| 6,619,055 B1 | 9/2003 | Addy | |

(56) References Cited

U.S. PATENT DOCUMENTS

| | | |
|---|---|---|
| 6,631,185 B1 | 10/2003 | Fleming, III |
| 6,639,517 B1 | 10/2003 | Chapman et al. |
| 6,645,066 B2 | 11/2003 | Gutta et al. |
| 6,666,086 B2 | 12/2003 | Colman et al. |
| 6,679,400 B1 | 1/2004 | Goodman |
| 6,704,681 B1 | 3/2004 | Nassof et al. |
| 6,714,977 B1 | 3/2004 | Fowler et al. |
| 6,731,215 B2 | 5/2004 | Harms et al. |
| 6,735,630 B1 | 5/2004 | Gelvin et al. |
| 6,748,804 B1 | 6/2004 | Lisec et al. |
| 6,759,956 B2 | 7/2004 | Menard et al. |
| 6,769,482 B2 | 8/2004 | Wagner et al. |
| 6,788,198 B2* | 9/2004 | Harshaw ................. 340/522 |
| 6,796,187 B2 | 9/2004 | Srinivasan et al. |
| 6,798,220 B1 | 9/2004 | Flanigan et al. |
| 6,826,948 B1 | 12/2004 | Bhatti et al. |
| 6,891,838 B1 | 5/2005 | Petite et al. |
| 6,892,751 B2 | 5/2005 | Sanders |
| 6,904,385 B1 | 6/2005 | Budike, Jr. |
| 6,935,570 B2 | 8/2005 | Acker, Jr. |
| 6,940,403 B2 | 9/2005 | Kail, IV |
| 6,990,821 B2 | 1/2006 | Singh et al. |
| 6,995,676 B2 | 2/2006 | Amacher |
| 7,024,336 B2 | 4/2006 | Salsbury et al. |
| 7,042,352 B2 | 5/2006 | Kates |
| 7,068,177 B2* | 6/2006 | Tice ................. 340/630 |
| 7,102,504 B2 | 9/2006 | Kates |
| 7,102,505 B2* | 9/2006 | Kates ................. 340/521 |
| 7,135,965 B2 | 11/2006 | Chapman, Jr. et al. |
| 7,142,107 B2 | 11/2006 | Kates |
| 7,142,123 B1 | 11/2006 | Kates |
| 7,149,727 B1 | 12/2006 | Nicholls et al. |
| 7,149,729 B2 | 12/2006 | Kaasten et al. |
| 7,188,482 B2 | 3/2007 | Sadegh et al. |
| 7,218,237 B2 | 5/2007 | Kates |
| 7,228,726 B2 | 6/2007 | Kates |
| 7,230,528 B2 | 6/2007 | Kates |
| 7,336,168 B2 | 2/2008 | Kates |
| 7,348,875 B2 | 3/2008 | Hughes et al. |
| 7,379,791 B2 | 5/2008 | Tamarkin et al. |
| RE40,437 E | 7/2008 | Rosen |
| 7,411,494 B2 | 8/2008 | Kates |
| 7,412,876 B2 | 8/2008 | Kates |
| 7,469,550 B2 | 12/2008 | Chapman, Jr. et al. |
| 7,528,711 B2 | 5/2009 | Kates |
| 7,623,028 B2* | 11/2009 | Kates ................. 340/521 |
| 7,644,869 B2 | 1/2010 | Hoglund et al. |
| 7,702,424 B2 | 4/2010 | Cannon et al. |
| 7,735,118 B2 | 6/2010 | Brok et al. |
| 7,784,704 B2 | 8/2010 | Harter |
| 7,802,618 B2 | 9/2010 | Simon et al. |
| 7,837,958 B2 | 11/2010 | Crapser et al. |
| 7,848,900 B2 | 12/2010 | Steinberg et al. |
| 7,849,698 B2 | 12/2010 | Harrod et al. |
| 7,854,389 B2 | 12/2010 | Ahmed |
| 7,975,292 B2 | 7/2011 | Corella |
| 8,010,237 B2 | 8/2011 | Cheung et al. |
| 8,019,567 B2 | 9/2011 | Steinberg et al. |
| 8,037,022 B2 | 10/2011 | Rahman et al. |
| 8,090,477 B1 | 1/2012 | Steinberg |
| 8,091,375 B2 | 1/2012 | Crawford |
| 8,131,497 B2 | 3/2012 | Steinberg et al. |
| 8,174,381 B2 | 5/2012 | Imes et al. |
| 8,180,492 B2 | 5/2012 | Steinberg |
| 8,219,249 B2 | 7/2012 | Harrod et al. |
| 8,234,694 B2 | 7/2012 | Youn et al. |
| 8,255,090 B2 | 8/2012 | Frader-Thompson et al. |
| 8,415,829 B2 | 4/2013 | Di Cristofaro |
| 8,442,752 B2 | 5/2013 | Wijaya et al. |
| 8,638,215 B2* | 1/2014 | Kates ................. 340/521 |
| 2002/0005707 A1 | 1/2002 | Kerai et al. |
| 2002/0011570 A1 | 1/2002 | Castleman |
| 2002/0033759 A1 | 3/2002 | Morello |
| 2002/0075145 A1 | 6/2002 | Hardman et al. |
| 2002/0084414 A1 | 7/2002 | Baker et al. |
| 2002/0118116 A1* | 8/2002 | Tice et al. ................. 340/632 |
| 2002/0186141 A1 | 12/2002 | Jen et al. |
| 2002/0198629 A1 | 12/2002 | Ellis |
| 2003/0011482 A1 | 1/2003 | Harms et al. |
| 2003/0058093 A1 | 3/2003 | Dohi et al. |
| 2003/0122677 A1 | 7/2003 | Kail, IV |
| 2003/0151513 A1 | 8/2003 | Herrmann et al. |
| 2003/0174056 A1* | 9/2003 | Harshaw ................. 340/522 |
| 2003/0199247 A1 | 10/2003 | Striemer |
| 2004/0007264 A1 | 1/2004 | Bootka |
| 2004/0090329 A1 | 5/2004 | Hitt |
| 2004/0117311 A1 | 6/2004 | Agarwal et al. |
| 2004/0249479 A1 | 12/2004 | Shorrock |
| 2004/0256472 A1 | 12/2004 | DeLuca |
| 2005/0012601 A1 | 1/2005 | Matsubara et al. |
| 2005/0035877 A1 | 2/2005 | Kim |
| 2005/0090915 A1 | 4/2005 | Geiwitz |
| 2005/0105841 A1 | 5/2005 | Luo et al. |
| 2005/0116667 A1 | 6/2005 | Mueller et al. |
| 2005/0125083 A1 | 6/2005 | Kiko |
| 2005/0128067 A1 | 6/2005 | Zakrewski |
| 2005/0131652 A1 | 6/2005 | Corwin et al. |
| 2005/0150968 A1 | 7/2005 | Shearer |
| 2005/0187867 A1 | 8/2005 | Sokolic et al. |
| 2005/0189429 A1 | 9/2005 | Breeden |
| 2005/0192915 A1 | 9/2005 | Ahmed et al. |
| 2005/0246408 A1 | 11/2005 | Chung |
| 2005/0258974 A1 | 11/2005 | Mahowald |
| 2005/0262923 A1 | 12/2005 | Kates |
| 2005/0270151 A1 | 12/2005 | Winick |
| 2005/0275527 A1 | 12/2005 | Kates |
| 2005/0275528 A1 | 12/2005 | Kates |
| 2005/0275529 A1 | 12/2005 | Kates |
| 2005/0275530 A1 | 12/2005 | Kates |
| 2005/0275547 A1 | 12/2005 | Kates |
| 2005/0280421 A1 | 12/2005 | Yomoda et al. |
| 2006/0007008 A1 | 1/2006 | Kates |
| 2006/0032379 A1 | 2/2006 | Kates |
| 2006/0059977 A1 | 3/2006 | Kates |
| 2006/0164257 A1 | 7/2006 | Giubbini |
| 2006/0186214 A1 | 8/2006 | Simon et al. |
| 2006/0196953 A1 | 9/2006 | Simon et al. |
| 2006/0208099 A1 | 9/2006 | Chapman et al. |
| 2006/0267756 A1 | 11/2006 | Kates |
| 2006/0273896 A1 | 12/2006 | Kates |
| 2007/0008157 A1* | 1/2007 | Siemens et al. ................. 340/577 |
| 2007/0038787 A1 | 2/2007 | Harris |
| 2007/0045431 A1 | 3/2007 | Chapman Jr. et al. |
| 2007/0063833 A1 | 3/2007 | Kates |
| 2007/0090946 A1 | 4/2007 | Kates |
| 2007/0115902 A1 | 5/2007 | Shamoon et al. |
| 2007/0139183 A1 | 6/2007 | Kates |
| 2007/0205297 A1 | 9/2007 | Finkam et al. |
| 2007/0211076 A1 | 9/2007 | Kates |
| 2007/0229237 A1 | 10/2007 | Kates |
| 2007/0234784 A1 | 10/2007 | Kates |
| 2007/0266575 A1 | 11/2007 | Nash |
| 2008/0015742 A1 | 1/2008 | Kulyk et al. |
| 2008/0141754 A1 | 6/2008 | Kates |
| 2008/0183335 A1 | 7/2008 | Poth et al. |
| 2008/0191045 A1 | 8/2008 | Harter |
| 2008/0273754 A1 | 11/2008 | Hick et al. |
| 2008/0278310 A1 | 11/2008 | Kates |
| 2008/0278315 A1 | 11/2008 | Kates |
| 2008/0278316 A1 | 11/2008 | Kates |
| 2008/0278342 A1 | 11/2008 | Kates |
| 2008/0284590 A1 | 11/2008 | Kates |
| 2008/0302172 A1 | 12/2008 | Kates |
| 2008/0303654 A1 | 12/2008 | Kates |
| 2008/0317292 A1 | 12/2008 | Baker et al. |
| 2009/0057427 A1 | 3/2009 | Geadelmann et al. |
| 2009/0070412 A1 | 3/2009 | D'Angelo et al. |
| 2009/0140868 A1* | 6/2009 | Booth ................. 340/628 |
| 2009/0143918 A1 | 6/2009 | Amundson et al. |
| 2009/0171862 A1 | 7/2009 | Harrod et al. |
| 2009/0192894 A1 | 7/2009 | Dikeman |
| 2009/0254225 A1 | 10/2009 | Boucher et al. |
| 2009/0259713 A1 | 10/2009 | Blumrich et al. |
| 2009/0297901 A1 | 12/2009 | Kilian et al. |

(56) References Cited

U.S. PATENT DOCUMENTS

| | | | |
|---|---|---|---|
| 2009/0327354 | A1 | 12/2009 | Resnick et al. |
| 2010/0019051 | A1 | 1/2010 | Rosen |
| 2010/0025483 | A1 | 2/2010 | Hoeynck et al. |
| 2010/0050004 | A1 | 2/2010 | Hamilton, II et al. |
| 2010/0058450 | A1 | 3/2010 | Fein et al. |
| 2010/0070084 | A1 | 3/2010 | Steinberg et al. |
| 2010/0070086 | A1 | 3/2010 | Harrod et al. |
| 2010/0070234 | A1 | 3/2010 | Steinberg et al. |
| 2010/0084482 | A1 | 4/2010 | Kennedy et al. |
| 2010/0156608 | A1 | 6/2010 | Bae et al. |
| 2010/0167783 | A1 | 7/2010 | Alameh et al. |
| 2010/0179704 | A1 | 7/2010 | Ozog |
| 2010/0199086 | A1 | 8/2010 | Kuang et al. |
| 2010/0211224 | A1 | 8/2010 | Keeling et al. |
| 2010/0262298 | A1 | 10/2010 | Johnson et al. |
| 2010/0262299 | A1 | 10/2010 | Cheung et al. |
| 2010/0271217 | A1 | 10/2010 | Kates |
| 2010/0280667 | A1 | 11/2010 | Steinberg |
| 2010/0289643 | A1 | 11/2010 | Trundle et al. |
| 2010/0308119 | A1 | 12/2010 | Steinberg et al. |
| 2010/0318227 | A1 | 12/2010 | Steinberg et al. |
| 2011/0046792 | A1 | 2/2011 | Imes et al. |
| 2011/0046805 | A1 | 2/2011 | Bedros et al. |
| 2011/0046806 | A1 | 2/2011 | Nagel et al. |
| 2011/0054710 | A1 | 3/2011 | Imes et al. |
| 2011/0077758 | A1 | 3/2011 | Tran et al. |
| 2011/0077896 | A1 | 3/2011 | Steinberg et al. |
| 2011/0078675 | A1 | 3/2011 | Van Camp et al. |
| 2011/0119747 | A1 | 5/2011 | Lambiase |
| 2011/0151837 | A1 | 6/2011 | Winbush, III |
| 2011/0160913 | A1 | 6/2011 | Parker et al. |
| 2011/0185895 | A1 | 8/2011 | Freen |
| 2011/0307103 | A1 | 12/2011 | Cheung et al. |
| 2011/0307112 | A1 | 12/2011 | Barrilleaux |
| 2012/0017611 | A1 | 1/2012 | Coffel et al. |
| 2012/0065935 | A1 | 3/2012 | Steinberg et al. |
| 2012/0085831 | A1 | 4/2012 | Kopp |
| 2012/0101637 | A1 | 4/2012 | Imes et al. |
| 2012/0158350 | A1 | 6/2012 | Steinberg et al. |
| 2012/0221151 | A1 | 8/2012 | Steinberg |
| 2012/0252430 | A1 | 10/2012 | Imes et al. |
| 2014/0320295 | A1 | 10/2014 | Kates |
| 2014/0333445 | A1 | 11/2014 | Kates |

FOREIGN PATENT DOCUMENTS

| | | |
|---|---|---|
| DE | 3415786 | 11/1984 |
| EP | 070449 | 1/1983 |
| EP | 093463 | 11/1983 |
| EP | 346152 | 12/1989 |
| EP | 346152 | 10/1990 |
| EP | 441999 | 8/1991 |
| EP | 196069 | 12/1991 |
| EP | 580298 | 1/1994 |
| EP | 930492 | 7/1999 |
| GB | 231458 | 1/1926 |
| GB | 2278471 | 11/1994 |
| JP | 59106311 | 6/1984 |
| JP | 01252850 | 10/1989 |
| JP | 09298780 | 11/1997 |
| WO | 0021047 | 4/2000 |
| WO | 0055825 | 9/2000 |
| WO | 03009631 | 1/2003 |
| WO | 2004010398 | 1/2004 |
| WO | 2004073326 | 8/2004 |
| WO | 2004100763 | 11/2004 |
| WO | 2005010837 | 2/2005 |

OTHER PUBLICATIONS

Braeburn 5300 Installer Guide, Braeburn Systems, LLC, Dec. 9, 2009, 10 pages.
Braeburn Model 5200, Braeburn Systems, LLC, Jul. 20, 2011, 11 pages.
Ecobee Smart Si Thermostat Installation Manual, Ecobee, Apr. 3, 2012, 40 pages.
Ecobee Smart Si Thermostat User Manual, Ecobee, Apr. 3, 2012, 44 pages.
Ecobee Smart Thermostat Installation Manual, Jun. 29, 2011, 20 pages.
Ecobee Smart Thermostat User Manual, May 11, 2010, 20 pages.
Electric Heat Lock Out on Heat Pumps, Washington State University Extension Energy Program, Apr. 2010, pp. 1-3.
Honeywell Installation Guide FocusPRO TH6000 Series, Honeywell International, Inc., Jan. 5, 2012, 24 pages.
Honeywell Operating Manual FocusPRO TH6000 Series, Honeywell International, Inc., Mar. 25, 2011, 80 pages.
Honeywell Prestige THX9321 and TXH9421 Product Data, Honeywell International, Inc., 68-0311, Jan. 2012, 126 pages.
Honeywell Prestige THX9321-9421 Operating Manual, Honeywell International, Inc., Jul. 6, 2011, 120 pages.
Hunter Internet Thermostat Installation Guide, Hunter Fan Co., Aug. 14, 2012, 8 pages.
Introducing the New Smart Si Thermostat, Datasheet [online]. Ecobee, Mar. 2012 [retrieved on Feb. 25, 2013]. Retrieved from the Internet: <URL: https://www.ecobee.com/solutions/home/smart-si/>, Mar. 12, 2012, 4 pages.
Lennox ComfortSense 5000 Owners Guide, Lennox Industries, Inc., Feb. 2008, 32 pages.
Lennox ComfortSense 7000 Owners Guide, Lennox Industries, Inc., May 2009, 15 pages.
Lennox iComfort Manual, Lennox Industries, Inc., Dec. 2010, 20 pages.
Lux PSPU732T Manual, LUX Products Corporation, Jan. 6, 2009, 48 pages.
NetX RP32-WIFI Network Thermostat Consumer Brochure, Network Thermostat, May 2011, 2 pages.
NetX RP32-WIFI Network Thermostat Specification Sheet, Network Thermostat, Feb. 28, 2012, 2 pages.
RobertShaw Product Manual 9620, Maple Chase Company, Jun. 12, 2001, 14 pages.
RobertShaw Product Manual 9825i2, Maple Chase Company, Jul. 17, 2006, 36 pages.
SYSTXCCUIZ01-V Infinity Control Installation Instructions, Carrier Corp, May 31, 2012, 20 pages.
T8611G Chronotherm IV Deluxe Programmable Heat Pump Thermostat Product Data, Honeywell International Inc., Oct. 1997, 24 pages.
TB-PAC, TB-PHP, Base Series Programmable Thermostats, Carrier Corp, May 14, 2012, 8 pages.
The Perfect Climate Comfort Center PC8900A W8900A-C Product Data Sheet, Honeywell International Inc, Apr. 2001, 44 pages.
TP-PAC, TP-PHP, TP-NAC, TP-NHP Performance Series AC/HP Thermostat Installation Instructions, Carrier Corp, Sep. 2007, 56 pages.
Trane Communicating Thermostats for Fan Coil, Trane, May 2011, 32 pages.
Trane Communicating Thermostats for Heat Pump Control, Trane, May 2011, 32 pages.
Trane Install XL600 Installation Manual, Trane, Mar. 2006, 16 pages.
Trane XL950 Installation Guide, Trane, Mar. 2011, 20 pages.
Venstar T2900 Manual, Venstar, Inc., Apr. 2008, 113 pages.
Venstar T5800 Manual, Venstar, Inc., Sep. 7, 2011, 63 pages.
VisionPRO TH8000 Series Installation Guide, Honeywell International, Inc., Jan. 2012, 12 pages.
VisionPRO TH8000 Series Operating Manual, Honeywell International, Inc., Mar. 2011, 96 pages.
VisionPRO Wi-Fi Programmable Thermostat User Guide, Honeywell International, Inc, Aug. 2012, 48 pages.
White Rodgers (Emerson) Model 1F81-261 Installation and Operating Instructions, White Rodgers, Apr. 15, 2010, 8 pages.
White Rodgers (Emerson) Model IF98EZ-1621 Homeowner's User Guide, White Rodgers, Jan. 25, 2012, 28 pages.
Akhlaghinia et al., Occupancy Monitoring in Intelligent Environment through Integrated Wireless Localizing Agents, IEEE, 2009, 7 pages.

(56) References Cited

OTHER PUBLICATIONS

Akhlaghinia et al., Occupant Behaviour Prediction in Ambient Intelligence Computing Environment, Journal of Uncertain Systems, vol. 2, No. 2, 2008, pp. 85-100.
Allen et al., Real-Time Earthquake Detection and Hazard Assessment by ElarmS Across California, Geophysical Research Letters, vol. 36, LOOB08, 2009, pp. 1-6.
Chatzigiannakis et al., Priority Based Adaptive Coordination of Wireless Sensors and Actors, Q2SWinet '06, Oct. 2006, pp. 37-44.
Deleeuw, Ecobee WiFi Enabled Smart Thermostat Part 2: The Features Review, retrieved from <URL: http://www.homenetworkenabled.com/content.php?136-ecobee-WiFi-enabled-Smart-Thermostat-Part-2-The-Features-review> [retrieved on Jan. 8, 2013], Dec. 2, 2011, 5 pages.
Gao et al., The Self-Programming TheArmostat: Optimizing Setback Schedules Based on Home Occupancy Patterns, In Proceedings of the First ACM Workshop on Embedded Sensing Systems for Energy-Efficiency in Buildings, Nov. 3, 2009, 6 pages.
Loisos et al., Buildings End-Use Energy Efficiency: Alternatives to Compressor Cooling, California Energy Commission, Public Interest Energy Research, Jan. 2000, 80 pages.
Lu et al., The Smart Thermostat: Using Occupancy Sensors to Save Energy in Homes, In Proceedings of the 8th ACM Conference on Embedded Networked Sensor Systems, Nov. 3-5, 2010, pp. 211-224.
Mozer, the Neural Network House: An Environmental that Adapts to its Inhabitants, Proceedings of the American Association for Artificial Intelligence SS-98-02, 1998, pp. 110-114.
Ros et al., Multi-Sensor Human Tracking with the Bayesian Occupancy Filter, IEEE, 2009, 8 pages.
Wong et al., Maximum Likelihood Estimation of Arma Model with Error Processes for Replicated Observations, National University of Singapore, Department of Economics, Working Paper No. 0217, Feb. 2002, pp. 1-19.
Winland Electronics, Inc. (2011). *Waterbug: Electronic water detection at its best*! [Brochure]. Mankato, Minnesota: Winland Electronics Inc. Retrieved from the Internet: <URL: www.winland.com>, 1 page.
GE General Eastern Instruments. *G-Cap™ 2 Relative Humidity Sensor* [Brochure]. GlobalSpec.com. Retrieved from the Internet: <URL: http://www.globalspec.com/FeaturedProducts/Detaii?ExhibitiD=1454> on Jun. 18, 2004, 2 pages.
Michell Instruments Ltd. *Impedance Moisture Sensor Technology* [Brochure]. Retrieved from the Internet: <URL: http://www.sensorland.com/HowPage029.html> on Jun. 18, 2004, 2 pages.
Indoor Health Products, Inc. (2001-2002). *Best Way to Control Indoor Molds, Dust Mites, and other Microorganisms: Measuring and Controlling Indoor Humidity* [Brochure]. Layton, Utah: Indoor Health Products, Inc. Retrieved from the Internet: <URL: http://www.relative-humidity-sensor.com> on Jun. 18, 2004, 3 pages.
Indoor Health Products, Inc. (2002). *Relative Humidity Information* [Brochure]. Layton, Utah: Indoor Health Products, Inc. Retrieved from the Internet: <URL: http://www.relative-humidity-sensor.com/relative-humidity.html> on Jun. 18, 2004, 6 pages.
Toxic Black Mold Information Center. (20002). *Ways to Prevent Mold Problems* [Brochure]. Layton, Utah: Toxic Black Mold Information Center. Retrieved from the Internet: <URL: http://www.toxic-black-mold-info.com/prevent.html> on Jun. 18, 2004, 12 pages.
U.S. Appl. No. 10/856,170, Notice of Allowance mailed on Dec. 13, 2005, 8 pages.
U.S. Appl. No. 10/856,231, Non-Final Office Action mailed on Apr. 5, 2006, 4 pages.
U.S. Appl. No. 10/856,231, Non-Final Office Action mailed on Dec. 21, 2005, 9 pages.
U.S. Appl. No. 10/856,231, Notice of Allowance mailed on Jun. 28, 2006, 4 pages.
U.S. Appl. No. 10/856,387, Non-Final Office Action mailed on Dec. 14, 2005, 10 pages.
U.S. Appl. No. 10/856,387, Notice of Allowance mailed on Jun. 23, 2006, 6 pages.
U.S. Appl. No. 10/856,390, Non-Final Office Action mailed on Dec. 15, 2005, 9 pages.
U.S. Appl. No. 10/856,390, Notice of Allowance mailed on Jun. 27, 2006, 7 pages.
U.S. Appl. No. 10/856,395, Final Office Action mailed on Oct. 30, 2006, 10 pages.
U.S. Appl. No. 10/856,395, Final Office Action mailed on Apr. 13, 2006, 8 pages.
U.S. Appl. No. 10/856,395, Non-Final Office Action mailed on Oct. 3, 2005, 7 pages.
U.S. Appl. No. 10/856,717, Non-Final Office Action mailed on Dec. 14, 2005, 8 pages.
U.S. Appl. No. 10/856,717, Non-Final Office Action mailed on May 31, 2006, 8 pages.
U.S. Appl. No. 10/856,717, Notice of Allowance mailed on Mar. 13, 2007, 6 pages.
U.S. Appl No. 10/948,628, Non-Final Office Action mailed on Sep. 8, 2006, 15 pages.
U.S. Appl. No. 10/948,628, Notice of Allowance mailed on Apr. 9, 2007, 6 pages.
U.S. Appl. No. 10/948,628, Restriction Requirement mailed on Dec. 30, 2005, 6 pages.
U.S. Appl. No. 10/948,628, Restriction Requirement mailed on Apr. 20, 2006, 7 pages.
U.S. Appl. No. 10/948,628, Supplemental Notice of Allowance mailed on May 3, 2007, 2 pages.
U.S. Appl. No. 11/145,880, Non-Final Office Action mailed on Mar. 1, 2007, 5 pages.
U.S. Appl. No. 11/145,880, Non-Final Office Action mailed on Apr. 27, 2006, 5 pages.
U.S. Appl. No. 11/145,880, Notice of Allowance mailed on Sep. 21, 2007, 4 pages.
U.S. Appl. No. 11/145,880, Notice of Allowance mailed on Jul. 5, 2007, 6 pages.
U.S. Appl. No. 11/145,880, Supplemental Notice of Allowance mailed on Dec. 10, 2007, 2 pages.
U.S. Appl. No. 11/216,225, Non-Final Office Action mailed on Mar. 4, 2008, 11 pages.
U.S. Appl. No. 11/216,225, Non-Final Office Action mailed on Jul. 10, 2008, 7 pages.
U.S. Appl. No. 11/216,225, Notice of Allowance mailed on Mar. 10, 2009, 9 pages.
U.S. Appl. No. 11/231,321, Non-Final Office Action mailed on Jul. 24, 2006, 9 pages.
U.S. Appl. No. 11/231,321, Notice of Allowance mailed on Mar. 21, 2007, 4 pages.
U.S. Appl. No. 11/233,931, Non-Final Office Action mailed on Jul. 10, 2006, 10 pages.
U.S. Appl. No. 11/233,931, Notice of Allowance mailed on Aug. 10, 2006, 8 pages.
U.S. Appl. No. 11/314,807, Final Office Action mailed on Apr. 1, 2008, 5 pages.
U.S. Appl. No. 11/314,807, Final Office Action Jul. 16, 2007, 5 pages.
U.S. Appl. No. 11/314,807, Non-Final Office Action mailed on Jan. 18, 2007, 6 pages.
U.S. Appl. No. 11/314,807, Notice of Allowance mailed on Dec. 24, 2008, 4 pages.
U.S. Appl. No. 11/494,988, Non Final Office Action mailed on Mar. 5, 2009, 8 pages.
U.S. Appl. No. 11/494,988, Notice of Allowance mailed on Jul. 17, 2009, 6 pages.
U.S. Appl. No. 11/562,313, Non-Final Office Action mailed on Sep. 5, 2007, 5 pages.
U.S. Appl. No. 11/562,313, Notice of Allowance mailed on May 23, 2008, 6 pages.
U.S. Appl. No. 11/562,313, Restriction Requirement mailed on Febraury 22, 2008, 5 pages.
U.S. Appl. No. 11/562,352, Final Office Action mailed on Aug. 21, 2008, 15 pages.
U.S. Appl. No. 11/562,352, Non-Final Office Action mailed on Jan. 14, 2008, 5 pages.

(56) References Cited

OTHER PUBLICATIONS

U.S. Appl. No. 11/748,388, Non-Final Office Action mailed on Dec. 17, 2008, 6 pages.
U.S. Appl. No. 11/748,388, Notice of Allowance mailed on May 19, 2009, 12 pages.
U.S. Appl. No. 11/761,760, Non-Final Office Action mailed on Jan. 16, 2008, 16 pages.
U.S. Appl. No. 11/761,760, Notice of Allowance mailed on Jul. 1, 2008, 6 pages.
U.S. Appl. No. 11/761,760, Restriction Requirement mailed on Oct. 11, 2007, 6 pages.
U.S. Appl. No. 12/036,915, Non-Final Office Action mailed on Oct. 8, 2008, 7 pages.
U.S. Appl. No. 12/193,641, Restriction Requirement mailed on Apr. 3, 2009, 7 pages.
U.S. Appl. No. 12/624,838, Non-Final Office Action mailed on Mar. 28, 2013, 7 pages.
U.S. Appl. No. 12/624,838, Notice of Allowance mailed on Oct. 4, 2013, 10 pages.
Texas Instruments, Inc. (1996). *Mechanical Data Sheet: PT (S-PQFP-G48) Plastic Quad Flatpack*, [Brochure]. Dallas, Texas: Texas Instruments, Inc., 2 pages.
Texas Instruments, Inc. (2001-2003). *TRF6901 Single-Chip RF Transceiver Product Catalog* [Brochure]. Dallas, Texas: Texas Instruments, Inc., 27 pages.

* cited by examiner

SYSTEM AND METHOD FOR HIGH-SENSITIVITY SENSOR

CROSS-REFERENCE TO RELATED APPLICATIONS

This application is a continuation of U.S. patent application Ser. No. 12/624,838, filed Nov. 24, 2009, and entitled, "SYSTEM AND METHOD FOR HIGH-SENSITIVITY SENSOR" now U.S. Pat. No. 8,638,215, which is a continuation of U.S. patent application Ser. No. 11/494,988, filed Jul. 28, 2006, and entitled "SYSTEM AND METHOD FOR HIGH-SENSITIVITY SENSOR" now U.S. Pat. No. 7,623,028, which is a continuation-in-part of U.S. patent application Ser. No. 10/856,390, filed May 27, 2004, and entitled "WIRELESS SENSOR SYSTEM", now U.S. Pat. No. 7,102,505. The entire disclosures of the above applications are hereby incorporated by reference, for all purposes, as if fully set forth herein.

BACKGROUND OF THE INVENTION

1. Field of the Invention

The present invention relates to a sensor with improved sensitivity for use in a wired or wireless sensor system for monitoring potentially dangerous or costly conditions, such as, for example, smoke, temperature, water, gas and the like.

2. Description of the Related Art

Maintaining and protecting a building or complex is difficult and costly. Some conditions, such as fires, gas leaks, etc., are a danger to the occupants and the structure. Other malfunctions, such as water leaks in roofs, plumbing, etc., are not necessarily dangerous for the occupants, but can, nevertheless, cause considerable damage. In many cases, an adverse condition such as water leakage, fire, etc., is not detected in the early stages when the damage and/or danger is relatively small. Sensors can be used to detect such adverse conditions, but sensors present their own set of problems. For example, adding sensors, such as, for example, smoke detectors, water sensors, and the like in an existing structure can be prohibitively expensive due to the cost of installing wiring between the remote sensors and a centralized monitoring device used to monitor the sensors. Adding wiring to provide power to the sensors further increases the cost. Moreover, with regard to fire sensors, most fire departments will not allow automatic notification of the fire department based on the data from a smoke detector alone. Most fire departments require that a specific temperature rate-of-rise be detected before an automatic fire alarm system can notify the fire department. Unfortunately, detecting fire by temperature rate-of-rise generally means that the fire is not detected until it is too late to prevent major damage.

Moreover, most sensors, such as smoke sensors, are configured with a fixed threshold. If the sensed quantity (e.g., smoke level) rises above the threshold, then an alarm is triggered. Unfortunately, the threshold level must be placed relatively high to avoid false alarms and to allow for natural aging of components, and to allow for natural variations in the ambient environment. Setting the threshold to a relatively high level avoids false alarms, but reduces the effectiveness of the sensor and can unnecessarily put people and property at risk.

SUMMARY

These and other problems are solved by a sensor unit that includes at least one sensor configured to measure an ambient condition and a controller. The controller can be configured to receive instructions, to report a notice level when the controller determines that data measured by the at least one sensor fails a report threshold test corresponding to a report threshold value. The controller can also be configured to obtain a plurality of calibration measurements from the at least one sensor during a calibration period and to adjust the threshold based on the calibration measurements. The controller can be configured to compute a first threshold level corresponding to background noise and a second threshold level corresponding to sensor noise, and to compute the report threshold value from the second threshold. In one embodiment, the sensor unit adjusts one or more of the thresholds based on ambient temperature.

In one embodiment, the sensor unit includes a fan controlled by the controller. The fan is configured to improve air exchange between a sensor chamber and ambient air. In one embodiment, the controller operates the fan during one or more measurement periods. In one embodiment, the controller operates the fan prior to one or more measurement periods.

In one embodiment, the controller reports a diagnostic error at least when the second threshold does not exceed the first threshold. In one embodiment, the controller reports a diagnostic error at least when the second threshold does not exceed the first threshold. In one embodiment, the controller measures the first threshold and the second threshold in response to a command. In one embodiment, the controller measures the first threshold and the second threshold at power-up (e.g., when a power source, such as, for example, batteries, line power etc., are provided to the sensor unit).

In one embodiment, the sensor system provides an adjustable threshold level for the sensed quantity. The adjustable threshold allows the sensor to adjust to ambient conditions, aging of components, and other operational variations while still providing a relatively sensitive detection capability for hazardous conditions. The adjustable threshold sensor can operate for an extended period of operability without maintenance or recalibration. In one embodiment, the sensor is self-calibrating and runs through a calibration sequence at startup or at periodic intervals. In one embodiment, the adjustable threshold sensor is used in an intelligent sensor system that includes one or more intelligent sensor units and a base unit that can communicate with the sensor units. When one or more of the sensor units detects an anomalous condition (e.g., smoke, fire, water, etc.) the sensor unit communicates with the base unit and provides data regarding the anomalous condition. The base unit can contact a supervisor or other responsible person by a plurality of techniques, such as, telephone, pager, cellular telephone, Internet (and/or local area network), etc. In one embodiment, one or more wireless repeaters are used between the sensor units and the base unit to extend the range of the system and to allow the base unit to communicate with a larger number of sensors.

In one embodiment, the adjustable-threshold sensor sets a threshold level according to an average value of the sensor reading. In one embodiment, the average value is a relatively long-term average. In one embodiment, the average is a time-weighted average wherein recent sensor readings used in the averaging process are weighted differently than less recent sensor readings. The average is used to set the threshold level. When the sensor reading rises above the threshold level, the sensor indicates an alarm condition. In one embodiment, the sensor indicates an alarm condition when the sensor reading rises above the threshold value for a specified period of time. In one embodiment, the sensor indicates an alarm condition when a statistical number of sensor readings (e.g., 3 of 2, 5 of 3, 10 of 7, etc.) are above the threshold level. In one embodiment, the sensor indicates various levels of alarm (e.g., notice, alert, alarm) based on how far above the threshold the sensor reading has risen and/or how rapidly the sensor reading has risen.

In one embodiment, the sensor system includes a number of sensor units located throughout a building that sense conditions and report anomalous results back to a central reporting station. The sensor units measure conditions that might indicate a fire, water leak, etc. The sensor units report the measured data to the base unit whenever the sensor unit determines that the measured data is sufficiently anomalous to be reported. The base unit can notify a responsible person such as, for example, a building manager, building owner, private security service, etc. In one embodiment, the sensor units do not send an alarm signal to the central location. Rather, the sensors send quantitative measured data (e.g., smoke density, temperature rate of rise, etc.) to the central reporting station.

In one embodiment, the sensor system includes a battery-operated sensor unit that detects a condition, such as, for example, smoke, temperature, humidity, moisture, water, water temperature, carbon monoxide, natural gas, propane gas, other flammable gases, radon, poison gasses, etc. The sensor unit is placed in a building, apartment, office, residence, etc. In order to conserve battery power, the sensor is normally placed in a low-power mode. In one embodiment, while in the low-power mode, the sensor unit takes regular sensor readings, adjusts the threshold level, and evaluates the readings to determine if an anomalous condition exists. If an anomalous condition is detected, then the sensor unit "wakes up" and begins communicating with the base unit or with a repeater. At programmed intervals, the sensor also "wakes up" and sends status information to the base unit (or repeater) and then listens for commands for a period of time.

In one embodiment, the sensor unit is bi-directional and configured to receive instructions from the central reporting station (or repeater). Thus, for example, the central reporting station can instruct the sensor to: perform additional measurements; go to a standby mode; wake up; report battery status; change wake-up interval; run self-diagnostics and report results; report its threshold level, change its threshold level, change its threshold calculation equation, change its alarm calculation equation, etc. In one embodiment, the sensor unit also includes a tamper switch. When tampering with the sensor is detected, the sensor reports such tampering to the base unit. In one embodiment, the sensor reports its general health and status to the central reporting station on a regular basis (e.g., results of self-diagnostics, battery health, etc.).

In one embodiment, the sensor unit provides two wake-up modes, a first wake-up mode for taking measurements (and reporting such measurements if deemed necessary), and a second wake-up mode for listening for commands from the central reporting station. The two wake-up modes, or combinations thereof, can occur at different intervals.

In one embodiment, the sensor units use spread-spectrum techniques to communicate with the base unit and/or the repeater units. In one embodiment, the sensor units use frequency-hopping spread-spectrum. In one embodiment, each sensor unit has an Identification code (ID) and the sensor units attaches its ID to outgoing communication packets. In one embodiment, when receiving wireless data, each sensor unit ignores data that is addressed to other sensor units.

The repeater unit is configured to relay communications traffic between a number of sensor units and the base unit. The repeater units typically operate in an environment with several other repeater units and thus, each repeater unit contains a database (e.g., a lookup table) of sensor IDs. During normal operation, the repeater only communicates with designated wireless sensor units whose IDs appears in the repeater's database. In one embodiment, the repeater is battery-operated and conserves power by maintaining an internal schedule of when its designated sensors are expected to transmit and going to a low-power mode when none of its designated sensor units is scheduled to transmit. In one embodiment, the repeater uses spread-spectrum to communicate with the base unit and the sensor units. In one embodiment, the repeater uses frequency-hopping spread-spectrum to communicate with the base unit and the sensor units. In one embodiment, each repeater unit has an ID and the repeater unit attaches its ID to outgoing communication packets that originate in the repeater unit. In one embodiment, each repeater unit ignores data that is addressed to other repeater units or to sensor units not serviced by the repeater.

In one embodiment, the repeater is configured to provide bi-directional communication between one or more sensors and a base unit. In one embodiment, the repeater is configured to receive instructions from the central reporting station (or repeater). Thus, for example, the central reporting station can instruct the repeater to: send commands to one or more sensors; go to standby mode; "wake up"; report battery status; change wake-up interval; run self-diagnostics and report results; etc.

The base unit is configured to receive measured sensor data from a number of sensor units. In one embodiment, the sensor information is relayed through the repeater units. The base unit also sends commands to the repeater units and/or sensor units. In one embodiment, the base unit includes a diskless PC that runs off of a CD-ROM, flash memory, DVD, or other read-only device, etc. When the base unit receives data from a wireless sensor indicating that there may be an emergency condition (e.g., a fire or excess smoke, temperature, water, flammable gas, etc.) the base unit will attempt to notify a responsible party (e.g., a building manager) by several communication channels (e.g., telephone, Internet, pager, cell phone, etc.). In one embodiment, the base unit sends instructions to place the wireless sensor in an alert mode (inhibiting the wireless sensor's low-power mode). In one embodiment, the base unit sends instructions to activate one or more additional sensors near the first sensor.

In one embodiment, the base unit maintains a database of the health, battery status, signal strength, and current operating status of all of the sensor units and repeater units in the wireless sensor system. In one embodiment, the base unit automatically performs routine maintenance by sending commands to each sensor to run a self-diagnostic and report the results. The base unit collects such diagnostic results. In one embodiment, the base unit sends instructions to each sensor telling the sensor how long to wait between "wakeup" intervals. In one embodiment, the base unit schedules different wakeup intervals to different sensors based on the sensor's health, battery health, location, etc. In one embodiment, the base unit sends instructions to repeaters to route sensor information around a failed repeater.

DETAILED DESCRIPTION

Figure 1:
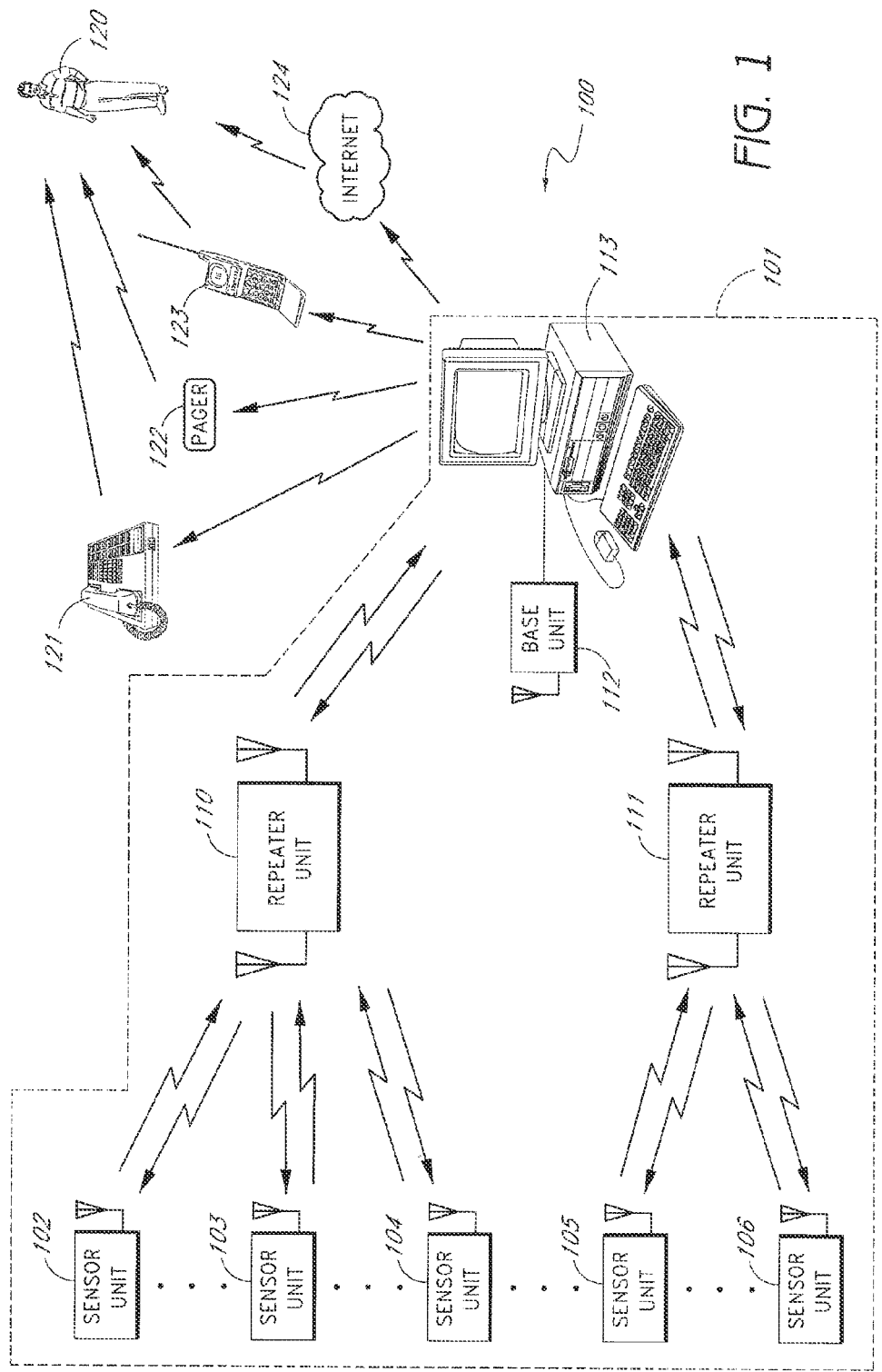
FIG. 1 shows sensor system that includes a plurality of sensor units that communicate with a base unit through a number of repeater units

FIG. 1 shows a sensor system 100 that includes a plurality of sensor units 102-106 that communicate with a base unit 112 through a number of repeater units 110-111. The sensor units 102-106 are located throughout a building 101. Sensor units 102-104 communicate with the repeater 110. Sensor units 105-106 communicate with the repeater 111. The repeaters 110-111 communicate with the base unit 112. The base unit 112 communicates with a monitoring computer system 113 through a computer network connection such as, for example, Ethernet, wireless Ethernet, firewire port, Universal Serial Bus (USB) port, bluetooth, etc. The computer system 113 contacts a building manager, maintenance service, alarm service, or other responsible personnel 120 using one or more of several communication systems such as, for example, telephone 121, pager 122, cellular telephone 123 (e.g., direct contact, voicemail, text, etc.), and/or through the Internet and/or local area network 124 (e.g., through email, instant messaging, network communications, etc.). In one embodiment, multiple base units 112 are provided to the monitoring computer 113. In one embodiment, the monitoring computer 113 is provided to more than one computer monitors, thus, allowing more data to be displayed than can conveniently be displayed on a single monitor. In one embodiment, the monitoring computer 113 is provided to multiple monitors located in different locations, thus allowing the data from the monitoring computer 113 to be displayed in multiple locations.

The sensor units 102-106 include sensors to measure conditions, such as, for example, smoke, temperature, moisture, water, water temperature, humidity, carbon monoxide, natural gas, propane gas, security alarms, intrusion alarms (e.g., open doors, broken windows, open windows, and the like), other flammable gases, radon, poison gasses, etc. Different sensor units can be configured with different sensors or with combinations of sensors. Thus, for example, in one installation the sensor units 102 and 104 could be configured with smoke and/or temperature sensors while the sensor unit 103 could be configured with a humidity sensor.

The discussion that follows generally refers to the sensor unit 102 as an example of a sensor unit, with the understanding that the description of the sensor unit 102 can be applied to many sensor units. Similarly, the discussion generally refers to the repeater 110 by way of example, and not limitation. It will also be understood by one of ordinary skill in the art that repeaters are useful for extending the range of the sensor units 102-106 but are not required in all embodiments. Thus, for example, in one embodiment, one or more of the sensor units 102-106 can communicate directly with the base unit 112 without going through a repeater. It will also be understood by one of ordinary skill in the art that FIG. 1 shows only five sensor units (102-106) and two repeater units (110-111) for purposes of illustration and not by way of limitation. An installation in a large apartment building or complex would typically involve many sensor units and repeater units. Moreover, one of ordinary skill in the art will recognize that one repeater unit can service relatively many sensor units. In one embodiment, the sensor units 102 can communicate directly with the base unit 112 without going through a repeater 111.

When the sensor unit 102 detects an anomalous condition (e.g., smoke, fire, water, etc.) the sensor unit communicates with the appropriate repeater unit 110 and provides data regarding the anomalous condition. The repeater unit 110 forwards the data to the base unit 112, and the base unit 112 forwards the information to the computer 113. The computer 113 evaluates the data and takes appropriate action. If the computer 113 determines that the condition is an emergency (e.g., fire, smoke, large quantities of water), then the computer 113 contacts the appropriate personnel 120. If the computer 113 determines that the situation warrants reporting, but is not an emergency, then the computer 113 logs the data for later reporting. In this way, the sensor system 100 can monitor the conditions in and around the building 101.

In one embodiment, the sensor unit 102 has an internal power source (e.g., battery, solar cell, fuel cell, etc.). In order to conserve power, the sensor unit 102 is normally placed in a low-power mode. In one embodiment, using sensors that require relatively little power, while in the low-power mode the sensor unit 102 takes regular sensor readings and evaluates the readings to determine if an anomalous condition exists. In one embodiment, using sensors that require relatively more power, while in the low-power mode, the sensor unit 102 takes and evaluates sensor readings at periodic intervals. If an anomalous condition is detected, then the sensor unit 102 "wakes up" and begins communicating with the base unit 112 through the repeater 110. At programmed intervals, the sensor unit 102 also "wakes up" and sends status information (e.g., power levels, self diagnostic information, etc.) to the base unit (or repeater) and then listens for commands for a period of time. In one embodiment, the sensor unit 102 also includes a tamper detector. When tampering with the sensor unit 102 is detected, the sensor unit 102 reports such tampering to the base unit 112.

In one embodiment, the sensor unit 102 provides bi-directional communication and is configured to receive data and/or instructions from the base unit 112. Thus, for example, the base unit 112 can instruct the sensor unit 102 to perform additional measurements, to go to a standby mode, to wake up, to report battery status, to change wake-up interval, to run self-diagnostics and report results, etc. In one embodiment, the sensor unit 102 reports its general health and status on a regular basis (e.g., results of self-diagnostics, battery health, etc.)

In one embodiment, the sensor unit 102 provides two wake-up modes, a first wake-up mode for taking measurements (and reporting such measurements if deemed necessary), and a second wake-up mode for listening for commands from the central reporting station. The two wake-up modes, or combinations thereof, can occur at different intervals.

In one embodiment, the sensor unit 102 uses spread-spectrum techniques to communicate with the repeater unit 110. In one embodiment, the sensor unit 102 uses frequency-hopping spread-spectrum. In one embodiment, the sensor unit 102 has an address or identification (ID) code that distinguishes the sensor unit 102 from the other sensor units. The sensor unit 102 attaches its ID to outgoing communication packets so that transmissions from the sensor unit 102 can be identified by the repeater 110. The repeater 110 attaches the ID of the sensor unit 102 to data and/or instructions that are transmitted to the sensor unit 102. In one embodiment, the sensor unit 102 ignores data and/or instructions that are addressed to other sensor units.

In one embodiment, the sensor unit 102 includes a reset function. In one embodiment, the reset function is activated by the reset switch 208. In one embodiment, the reset function is active for a prescribed interval of time. During the reset interval, the transceiver 203 is in a receiving mode and can receive the identification code from an external programmer. In one embodiment, the external programmer wirelessly transmits a desired identification code. In one embodiment, the identification code is programmed by an external programmer that is connected to the sensor unit 102 through an electrical connector. In one embodiment, the electrical connection to the sensor unit 102 is provided by sending modulated control signals (power line carrier signals) through a connector used to connect the power source 206. In one embodiment, the external programmer provides power and control signals. In one embodiment, the external programmer also programs the type of sensor(s) installed in the sensor unit. In one embodiment, the identification code includes an area code (e.g., apartment number, zone number, floor number, etc.) and a unit number (e.g., unit 1, 2, 3, etc.).

In one embodiment, the sensor communicates with the repeater on the 900 MHz band. This band provides good transmission through walls and other obstacles normally found in and around a building structure. In one embodiment, the sensor communicates with the repeater on bands above and/or below the 900 MHz band. In one embodiment, the sensor, repeater, and/or base unit listens to a radio frequency channel before transmitting on that channel or before beginning transmission. If the channel is in use, (e.g., by another device such as another repeater, a cordless telephone, etc.) then the sensor, repeater, and/or base unit changes to a different channel. In one embodiment, the sensor, repeater, and/or base unit coordinate frequency hopping by listening to radio frequency channels for interference and using an algorithm to select a next channel for transmission that avoids the interference. Thus, for example, in one embodiment, if a sensor senses a dangerous condition and goes into a continuous transmission mode, the sensor will test (e.g., listen to) the channel before transmission to avoid channels that are blocked, in use, or jammed. In one embodiment, the sensor continues to transmit data until it receives an acknowledgement from the base unit that the message has been received. In one embodiment, the sensor transmits data having a normal priority (e.g., status information) and does not look for an acknowledgement, and the sensor transmits data having elevated priority (e.g., excess smoke, temperature, etc.) until an acknowledgement is received.

The repeater unit 110 is configured to relay communications traffic between the sensor 102 (and similarly, the sensor units 103-104) and the base unit 112. The repeater unit 110 typically operates in an environment with several other repeater units (such as the repeater unit 111 in FIG. 1) and thus, the repeater unit 110 contains a database (e.g., a lookup table) of sensor unit IDs. In FIG. 1, the repeater 110 has database entries for the IDs of the sensors 102-104, and thus, the sensor 110 will only communicate with sensor units 102-104. In one embodiment, the repeater 110 has an internal power source (e.g., battery, solar cell, fuel cell, etc.) and conserves power by maintaining an internal schedule of when the sensor units 102-104 are expected to transmit. In one embodiment, the repeater unit 110 goes to a low-power mode when none of its designated sensor units is scheduled to transmit. In one embodiment, the repeater 110 uses spread-spectrum techniques to communicate with the base unit 112 and with the sensor units 102-104. In one embodiment, the repeater 110 uses frequency-hopping spread-spectrum to communicate with the base unit 112 and the sensor units 102-104. In one embodiment, the repeater unit 110 has an address or identification (ID) code and the repeater unit 110 attaches its address to outgoing communication packets that originate in the repeater (that is, packets that are not being forwarded). In one embodiment, the repeater unit 110 ignores data and/or instructions that are addressed to other repeater units or to sensor units not serviced by the repeater 110.

In one embodiment, the base unit 112 communicates with the sensor unit 102 by transmitting a communication packet addressed to the sensor unit 102. The repeaters 110 and 111 both receive the communication packet addressed to the sensor unit 102. The repeater unit 111 ignores the communication packet addressed to the sensor unit 102. The repeater unit 110 transmits the communication packet addressed to the sensor unit 102. In one embodiment, the sensor unit 102, the repeater unit 110, and the base unit 112 communicate using Frequency-Hopping Spread Spectrum (FHSS), also known as channel-hopping.

Frequency-hopping wireless systems offer the advantage of avoiding other interfering signals and avoiding collisions. Moreover, there are regulatory advantages given to systems that do not transmit continuously at one frequency. Channel-hopping transmitters change frequencies after a period of continuous transmission, or when interference is encountered. These systems may have higher transmit power and relaxed limitations on in-band spurs. FCC regulations limit transmission time on one channel to 400 milliseconds (averaged over 10-20 seconds depending on channel bandwidth) before the transmitter must change frequency. There is a minimum frequency step when changing channels to resume transmission. If there are 25 to 49 frequency channels, regulations allow effective radiated power of 24 dBm, spurs must be −20 dBc, and harmonics must be −41.2 dBc. With 50 or more channels, regulations allow effective radiated power to be up to 30 dBm.

In one embodiment, the sensor unit 102, the repeater unit 110, and the base unit 112 communicate using FHSS wherein the frequency hopping of the sensor unit 102, the repeater unit 110, and the base unit 112 are not synchronized such that at any given moment, the sensor unit 102 and the repeater unit 110 are on different channels. In such a system, the base unit 112 communicates with the sensor unit 102 using the hop frequencies synchronized to the repeater unit 110 rather than the sensor unit 102. The repeater unit 110 then forwards the data to the sensor unit using hop frequencies synchronized to the sensor unit 102. Such a system largely avoids collisions between the transmissions by the base unit 112 and the repeater unit 110.

In one embodiment, the sensor units 102-106 all use FHSS and the sensor units 102-106 are not synchronized. Thus, at any given moment, it is unlikely that any two or more of the sensor units 102-106 will transmit on the same frequency. In this manner, collisions are largely avoided. In one embodiment, collisions are not detected but are tolerated by the system 100. If a collision does occur, data lost due to the collision is effectively re-transmitted the next time the sensor units transmit sensor data. When the sensor units 102-106 and repeater units 110-111 operate in asynchronous mode, then a second collision is highly unlikely because the units causing the collisions have hopped to different channels. In one embodiment, the sensor units 102-106, repeater units 110-

111, and the base unit 112 use the same hop rate. In one embodiment, the sensor units 102-106, repeater units 110-111, and the base unit 112 use the same pseudo-random algorithm to control channel hopping, but with different starting seeds. In one embodiment, the starting seed for the hop algorithm is calculated from the ID of the sensor units 102-106, repeater units 110-111, or the base unit 112.

In an alternative embodiment, the base unit communicates with the sensor unit 102 by sending a communication packet addressed to the repeater unit 110, where the packet sent to the repeater unit 110 includes the address of the sensor unit 102. The repeater unit 102 extracts the address of the sensor unit 102 from the packet and creates and transmits a packet addressed to the sensor unit 102.

In one embodiment, the repeater unit 110 is configured to provide bi-directional communication between its sensors and the base unit 112. In one embodiment, the repeater 110 is configured to receive instructions from the base unit 110. Thus, for example, the base unit 112 can instruct the repeater to: send commands to one or more sensors; go to standby mode; "wake up"; report battery status; change wake-up interval; run self-diagnostics and report results; etc.

The base unit 112 is configured to receive measured sensor data from a number of sensor units either directly, or through the repeaters 110-111. The base unit 112 also sends commands to the repeater units 110-111 and/or to the sensor units 102-106. In one embodiment, the base unit 112 communicates with a diskless computer 113 that runs off of a CD-ROM. When the base unit 112 receives data from a sensor unit 102-106 indicating that there may be an emergency condition (e.g., a fire or excess smoke, temperature, water, etc.) the computer 113 will attempt to notify the responsible party 120.

In one embodiment, the computer 112 maintains a database of the health, power status (e.g., battery charge), and current operating status of all of the sensor units 102-106 and the repeater units 110-111. In one embodiment, the computer 113 automatically performs routine maintenance by sending commands to each sensor unit 102-106 to run a self-diagnostic and report the results. The computer 113 collects and logs such diagnostic results. In one embodiment, the computer 113 sends instructions to each sensor unit 102-106 telling the sensor how long to wait between "wakeup" intervals. In one embodiment, the computer 113 schedules different wakeup intervals to different sensor unit 102-106 based on the sensor unit's health, power status, location, etc. In one embodiment, the computer 113 schedules different wakeup intervals to different sensor unit 102-106 based on the type of data and urgency of the data collected by the sensor unit (e.g., sensor units that have smoke and/or temperature sensors produce data that should be checked relatively more often than sensor units that have humidity or moisture sensors). In one embodiment, the base unit sends instructions to repeaters to route sensor information around a failed repeater.

In one embodiment, the computer 113 produces a display that tells maintenance personnel which sensor units 102-106 need repair or maintenance. In one embodiment, the computer 113 maintains a list showing the status and/or location of each sensor according to the ID of each sensor.

In one embodiment, the sensor units 102-106 and/or the repeater units 110-111 measure the signal strength of the wireless signals received (e.g., the sensor unit 102 measures the signal strength of the signals received from the repeater unit 110, the repeater unit 110 measures the signal strength received from the sensor unit 102 and/or the base unit 112). The sensor units 102-106 and/or the repeater units 110-111 report such signal strength measurement back to the computer 113. The computer 113 evaluates the signal strength measurements to ascertain the health and robustness of the sensor system 100. In one embodiment, the computer 113 uses the signal strength information to re-route wireless communications traffic in the sensor system 100. Thus, for example, if the repeater unit 110 goes offline or is having difficulty communicating with the sensor unit 102, the computer 113 can send instructions to the repeater unit 111 to add the ID of the sensor unit 102 to the database of the repeater unit 111 (and similarly, send instructions to the repeater unit 110 to remove the ID of the sensor unit 102), thereby routing the traffic for the sensor unit 102 through the router unit 111 instead of the router unit 110.

Figure 2:
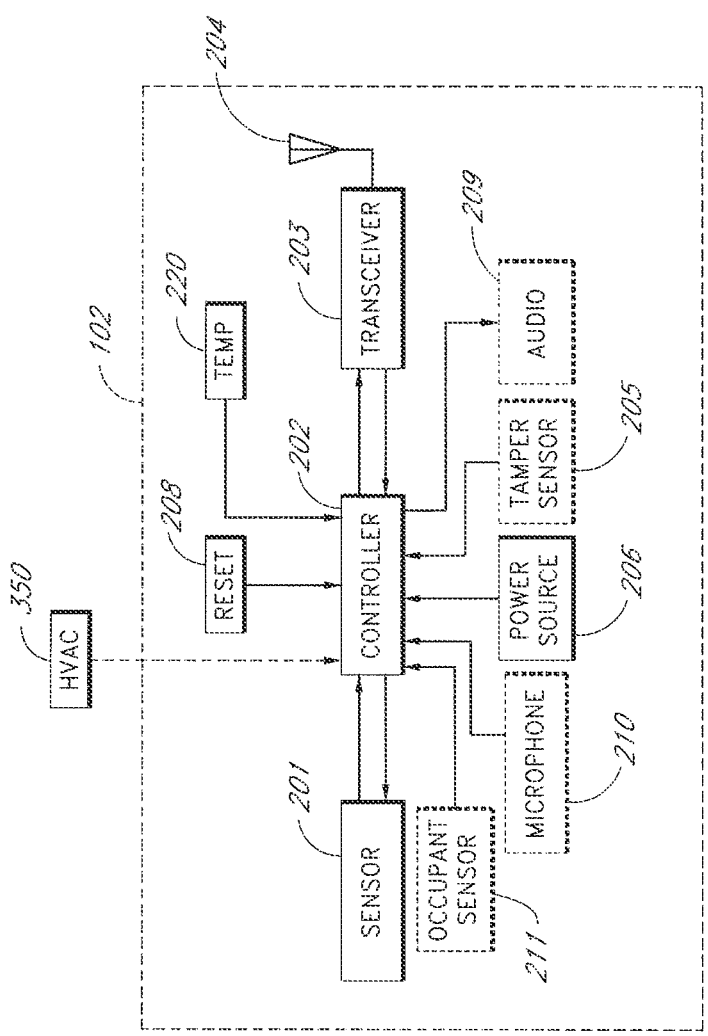
FIG. 2 is a block diagram of a sensor unit.

FIG. 2 is a block diagram of the sensor unit 102. In the sensor unit 102, one or more sensors 201 and a transceiver 203 are provided to a controller 202. The controller 202 typically provides power, data, and control information to the sensor(s) 201 and the transceiver 203. A power source 206 is provided to the controller 202. An optional tamper sensor 205 is also provided to the controller 202. A reset device (e.g., a switch) 208 is proved to the controller 202. In one embodiment, an optional audio output device 209 is provided. In one embodiment, the sensor 201 is configured as a plug-in module that can be replaced relatively easily. In one embodiment, a temperature sensor 220 is provided to the controller 202. In one embodiment, the temperature sensor 220 is configured to measure ambient temperature.

In one embodiment, the transceiver 203 is based on a TRF 6901 transceiver chip from Texas Instruments, Inc. In one embodiment, the controller 202 is a conventional programmable microcontroller. In one embodiment, the controller 202 is based on a Field Programmable Gate Array (FPGA), such as, for example, provided by Xilinx Corp. In one embodiment, the sensor 201 includes an optoelectric smoke sensor with a smoke chamber. In one embodiment, the sensor 201 includes a thermistor. In one embodiment, the sensor 201 includes a humidity sensor. In one embodiment, the sensor 201 includes a sensor, such as, for example, a water level sensor, a water temperature sensor, a carbon monoxide sensor, a moisture sensor, a water flow sensor, natural gas sensor, propane sensor, etc.

The controller 202 receives sensor data from the sensor(s) 201. Some sensors 201 produce digital data. However, for many types of sensors 201, the sensor data is analog data. Analog sensor data is converted to digital format by the controller 202. In one embodiment, the controller evaluates the data received from the sensor(s) 201 and determines whether the data is to be transmitted to the base unit 112. The sensor unit 102 generally conserves power by not transmitting data that falls within a normal range. In one embodiment, the controller 202 evaluates the sensor data by comparing the data value to a threshold value (e.g., a high threshold, a low threshold, or a high-low threshold). If the data is outside the threshold (e.g., above a high threshold, below a low threshold, outside an inner range threshold, or inside an outer range threshold), then the data is deemed to be anomalous and is transmitted to the base unit 112. In one embodiment, the data threshold is programmed into the controller 202. In one embodiment, the data threshold is programmed by the base unit 112 by sending instructions to the controller 202. In one embodiment, the controller 202 obtains sensor data and transmits the data when commanded by the computer 113.

In one embodiment, the tamper sensor 205 is configured as a switch that detects removal of/or tampering with the sensor unit 102.

Figure 3:
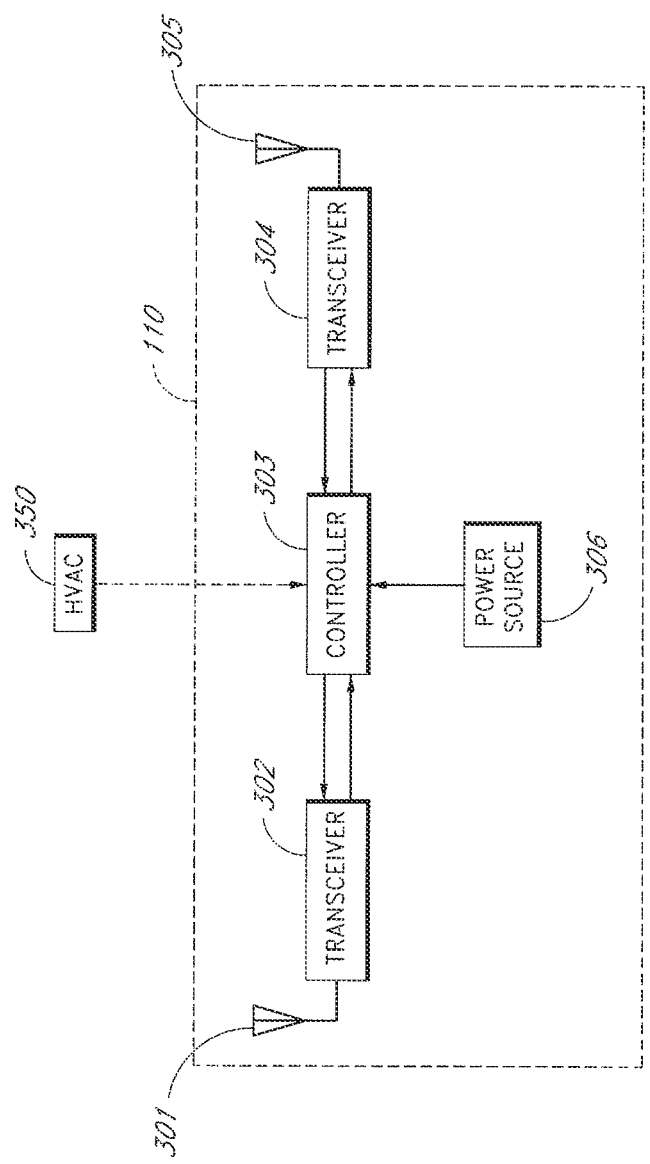
FIG. 3 is a block diagram of a repeater unit.

FIG. 3 is a block diagram of the repeater unit 110. In the repeater unit 110, a first transceiver 302 and a second transceiver 304 are provided to a controller 303. The controller 303 typically provides power, data, and control information to the transceivers 302, 304. A power source 306 is provided to the controller 303. An optional tamper sensor (not shown) is also provided to the controller 303.

When relaying sensor data to the base unit 112, the controller 303 receives data from the first transceiver 302 and provides the data to the second transceiver 304. When relaying instructions from the base unit 112 to a sensor unit, the controller 303 receives data from the second transceiver 304 and provides the data to the first transceiver 302. In one embodiment, the controller 303 conserves power by powering-down the transceivers 302, 304 during periods when the controller 303 is not expecting data. The controller 303 also monitors the power source 306 and provides status information, such as, for example, self-diagnostic information and/or information about the health of the power source 306, to the base unit 112. In one embodiment, the controller 303 sends status information to the base unit 112 at regular intervals. In one embodiment, the controller 303 sends status information to the base unit 112 when requested by the base unit 112. In one embodiment, the controller 303 sends status information to the base unit 112 when a fault condition (e.g., battery low) is detected.

In one embodiment, the controller 303 includes a table or list of identification codes for wireless sensor units 102. The repeater 110 forwards packets received from, or sent to, sensor units 102 in the list. In one embodiment, the repeater 110 receives entries for the list of sensor units from the computer 113. In one embodiment, the controller 303 determines when a transmission is expected from the sensor units 102 in the table of sensor units and places the repeater 110 (e.g., the transceivers 302, 304) in a low-power mode when no transmissions are expected from the transceivers on the list. In one embodiment, the controller 303 recalculates the times for low-power operation when a command to change reporting interval is forwarded to one of the sensor units 102 in the list (table) of sensor units or when a new sensor unit is added to the list (table) of sensor units.

Figure 4:
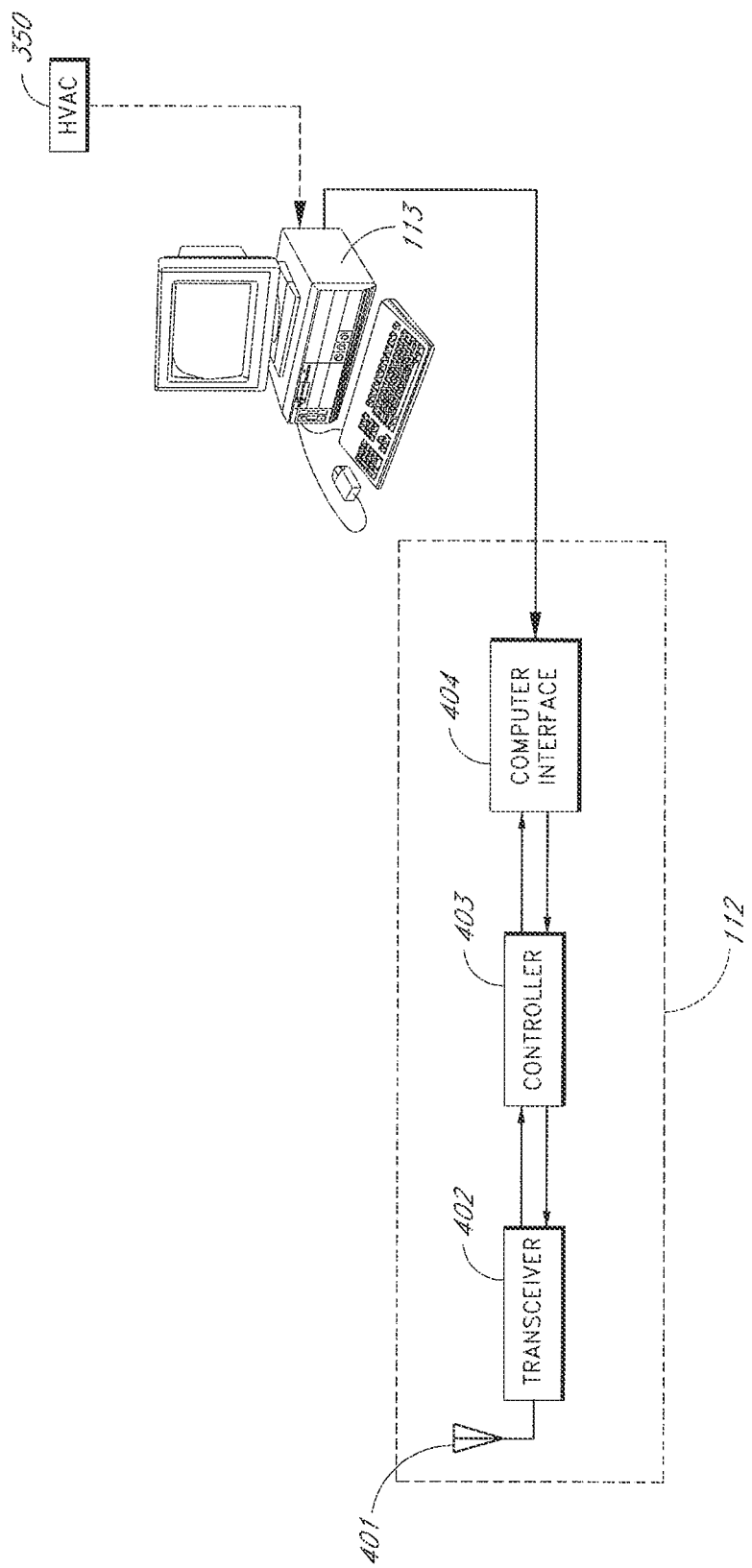
FIG. 4 is a block diagram of the base unit.

FIG. 4 is a block diagram of the base unit 112. In the base unit 112, a transceiver 402 and a computer interface 404 are provided to a controller 403. The controller 403 typically provides data and control information to the transceivers 402 and to the interface. The interface 404 is provided to a port on the monitoring computer 113. The interface 404 can be a standard computer data interface, such as, for example, Ethernet, wireless Ethernet, firewire port, Universal Serial Bus (USB) port, bluetooth, etc.

Figure 5:
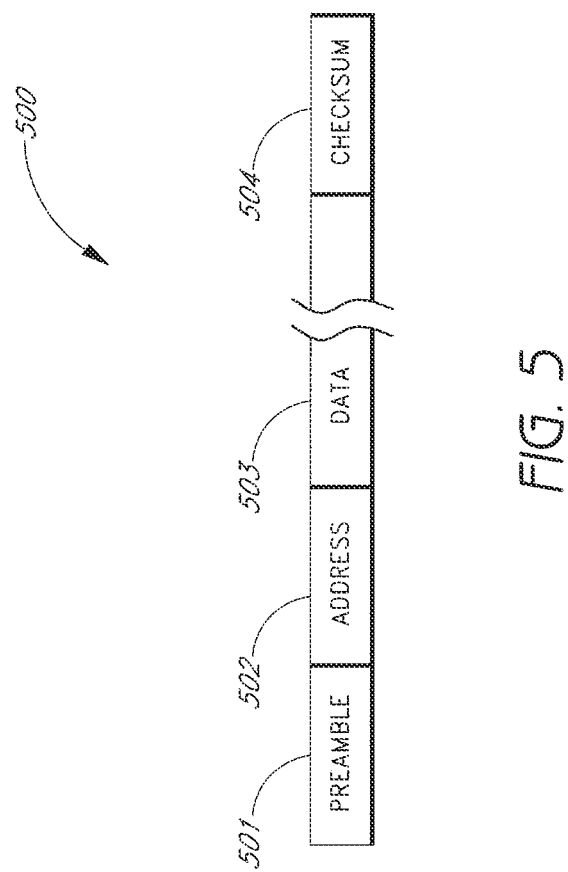
FIG. 5 shows a network communication packet used by the sensor units, repeater units, and the base unit.

FIG. 5 shows a communication packet 500 used by the sensor units, repeater units, and the base unit. The packet 500 includes a preamble portion 501, an address (or ID) portion 502, a data payload portion 503, and an integrity portion 504. In one embodiment, the integrity portion 504 includes a checksum. In one embodiment, the sensor units 102-106, the repeater units 110-111, and the base unit 112 communicate using packets such as the packet 500. In one embodiment, the packets 500 are transmitted using FHSS.

In one embodiment, the data packets that travel between the sensor unit 102, the repeater unit 111, and the base unit 112 are encrypted. In one embodiment, the data packets that travel between the sensor unit 102, the repeater unit 111, and the base unit 112 are encrypted and an authentication code is provided in the data packet so that the sensor unit 102, the repeater unit, and/or the base unit 112 can verify the authenticity of the packet.

In one embodiment the address portion 502 includes a first code and a second code. In one embodiment, the repeater 111 only examines the first code to determine if the packet should be forwarded. Thus, for example, the first code can be interpreted as a building (or building complex) code and the second code interpreted as a subcode (e.g., an apartment code, area code, etc.). A repeater that uses the first code for forwarding, thus, forwards packets having a specified first code (e.g., corresponding to the repeater's building or building complex). Thus, alleviates the need to program a list of sensor units 102 into a repeater, since a group of sensors in a building will typically all have the same first code but different second codes. A repeater so configured, only needs to know the first code to forward packets for any repeater in the building or building complex. This does, however, raise the possibility that two repeaters in the same building could try to forward packets for the same sensor unit 102. In one embodiment, each repeater waits for a programmed delay period before forwarding a packet. Thus, reducing the chance of packet collisions at the base unit (in the case of sensor unit to base unit packets) and reducing the chance of packet collisions at the sensor unit (in the case of base unit to sensor unit packets). In one embodiment, a delay period is programmed into each repeater. In one embodiment, delay periods are pre-programmed onto the repeater units at the factory or during installation. In one embodiment, a delay period is programmed into each repeater by the base unit 112. In one embodiment, a repeater randomly chooses a delay period. In one embodiment, a repeater randomly chooses a delay period for each forwarded packet. In one embodiment, the first code is at least 6 digits. In one embodiment, the second code is at least 5 digits.

In one embodiment, the first code and the second code are programmed into each sensor unit at the factory. In one embodiment, the first code and the second code are programmed when the sensor unit is installed. In one embodiment, the base unit 112 can re-program the first code and/or the second code in a sensor unit.

In one embodiment, collisions are further avoided by configuring each repeater unit 111 to begin transmission on a different frequency channel. Thus, if two repeaters attempt to begin transmission at the same time, the repeaters will not interfere with each other because the transmissions will begin on different channels (frequencies).

Figure 6:
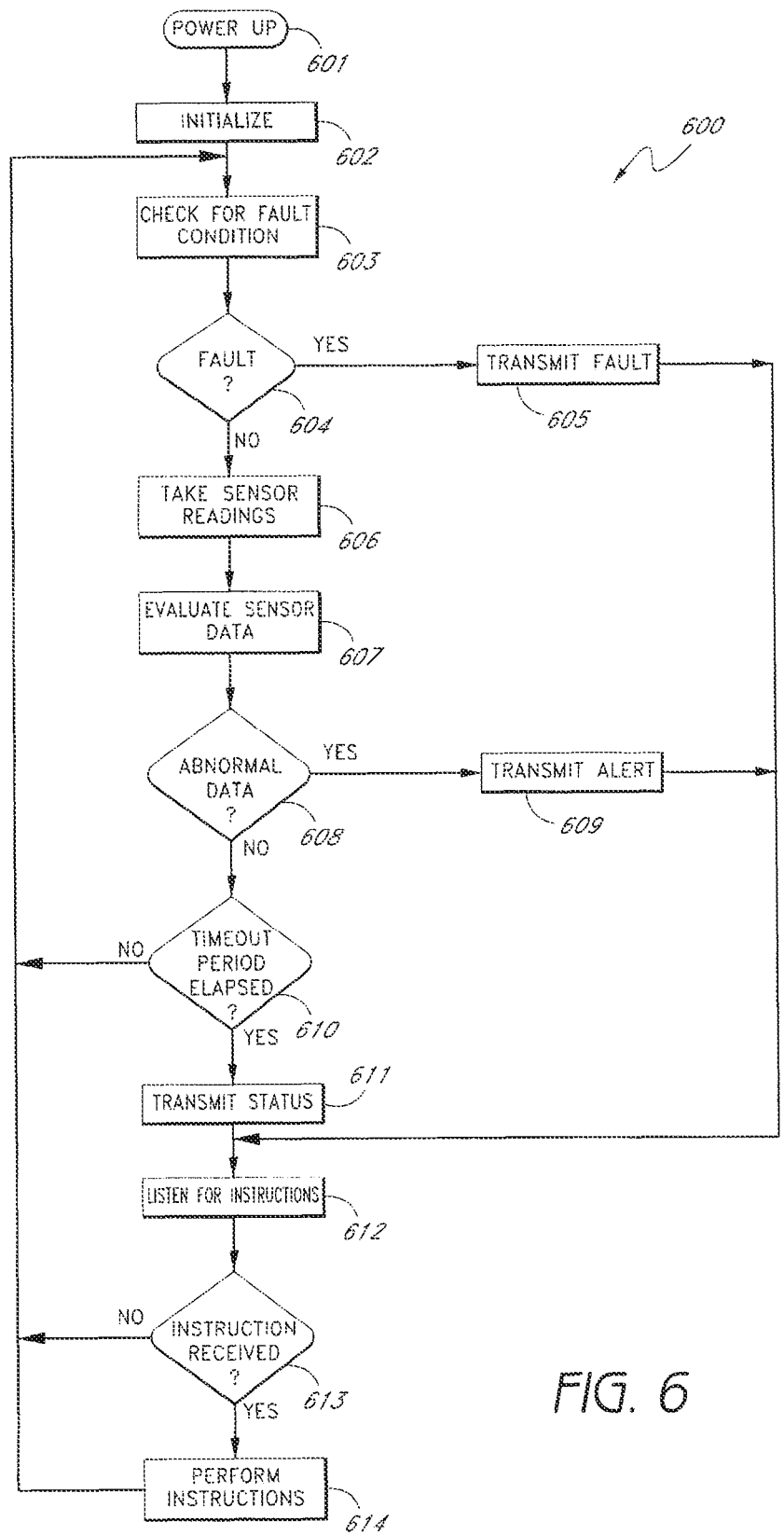
FIG. 6 is a flowchart showing operation of a sensor unit that provides relatively continuous monitoring.

FIG. 6 is a flowchart showing one embodiment of the operation of the sensor unit 102 wherein relatively continuous monitoring is provided. In FIG. 6, a power up block 601 is followed by an initialization block 602. After initialization, the sensor unit 102 checks for a fault condition (e.g., activation of the tamper sensor, low battery, internal fault, etc.) in a block 603. A decision block 604 checks the fault status. If a fault has occurred, then the process advances to a block 605 were the fault information is transmitted to the repeater 110 (after which, the process advances to a block 612); otherwise, the process advances to a block 606. In the block 606, the sensor unit 102 takes a sensor reading from the sensor(s) 201. The sensor data is subsequently evaluated in a block 607. If the sensor data is abnormal, then the process advances to a transmit block 609 where the sensor data is transmitted to the repeater 110 (after which, the process advances to a block 612); otherwise, the process advances to a timeout decision block 610. If the timeout period has not elapsed, then the process returns to the fault-check block 603; otherwise, the process advances to a transmit status block 611 where normal status information is transmitted to the repeater 110. In one embodiment, the normal status information transmitted is analogous to a simple "ping" which indicates that the sensor unit 102 is functioning normally. After the block 611, the process proceeds to a block 612 where the sensor unit 102 momentarily listens for instructions from the monitor computer 113. If an instruction is received, then the sensor unit 102 performs the instructions, otherwise, the process returns to the status check block 603. In one embodiment, transceiver 203 is normally powered down. The controller 202 powers up the transceiver 203 during execution of the blocks 605, 609, 611, and 612. The monitoring computer 113 can send instructions to the sensor unit 102 to change the parameters used to evaluate data used in block 607, the listen period used in block 612, etc.

Figure 7:
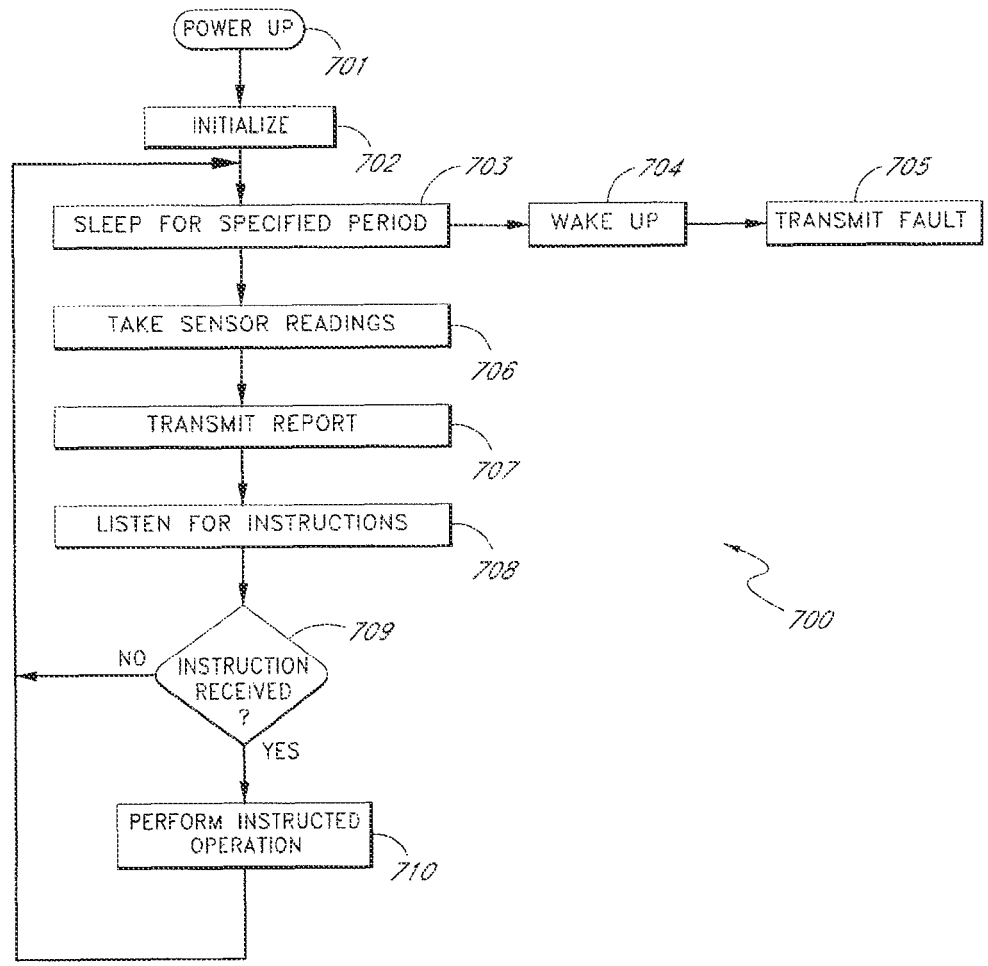
FIG. 7 is a flowchart showing operation of a sensor unit that provides periodic monitoring.

Relatively continuous monitoring, such as shown in FIG. 6, is appropriate for sensor units that sense relatively high-priority data (e.g., smoke, fire, carbon monoxide, flammable gas, etc.). By contrast, periodic monitoring can be used for sensors that sense relatively lower priority data (e.g., humidity, moisture, water usage, etc.). FIG. 7 is a flowchart showing one embodiment of operation of the sensor unit 102 wherein periodic monitoring is provided. In FIG. 7, a power up block 701 is followed by an initialization block 702. After initialization, the sensor unit 102 enters a low-power sleep mode 703. If a fault occurs during the sleep mode 703 (e.g., the tamper sensor is activated), then the process enters a wake-up block 704 followed by a transmit fault block 705. If no fault occurs during the sleep period, then when the specified sleep period has expired, the process enters a block 706 where the sensor unit 102 takes a sensor reading from the sensor(s) 201. The sensor data is subsequently sent to the monitoring computer 113 in a report block 707. After reporting, the sensor unit 102 enters a listen block 708 where the sensor unit 102 listens for a relatively short period of time for instructions from monitoring computer. If an instruction is received, then the sensor unit 102 performs the instructions, otherwise, the process returns to the sleep block 703. In one embodiment, the sensor 201 and transceiver 203 are normally powered down. The controller 202 powers up the sensor 201 during execution of the block 706. The controller 202 powers up the transceiver during execution of the blocks 705, 707, and 708. The monitoring computer 113 can send instructions to the sensor unit 102 to change the sleep period used in block 703, the listen period used in block 708, etc.

In one embodiment, the sensor unit transmits sensor data until a handshaking-type acknowledgement is received. Thus, rather than sleep if no instructions or acknowledgements are received after transmission (e.g., after the decision block 613 or 709) the sensor unit 102 retransmits its data and waits for an acknowledgement. The sensor unit 102 continues to transmit data and wait for an acknowledgement until an acknowledgement is received. In one embodiment, the sensor unit accepts an acknowledgement from a repeater unit 111 and it then becomes the responsibility of the repeater unit 111 to make sure that the data is forwarded to the base unit 112. In one embodiment, the repeater unit 111 does not generate the acknowledgement, but rather forwards an acknowledgement from the base unit 112 to the sensor unit 102. The two-way communication ability of the sensor unit 102 provides the capability for the base unit 112 to control the operation of the sensor unit 102 and also provides the capability for robust handshaking-type communication between the sensor unit 102 and the base unit 112.

Regardless of the normal operating mode of the sensor unit 102 (e.g., using the Flowcharts of FIGS. 6, 7, or other modes) in one embodiment, the monitoring computer 113 can instruct the sensor unit 102 to operate in a relatively continuous mode where the sensor repeatedly takes sensor readings and transmits the readings to the monitoring computer 113. Such a mode would can be used, for example, when the sensor unit 102 (or a nearby sensor unit) has detected a potentially dangerous condition (e.g., smoke, rapid temperature rise, etc.)

Figure 8:
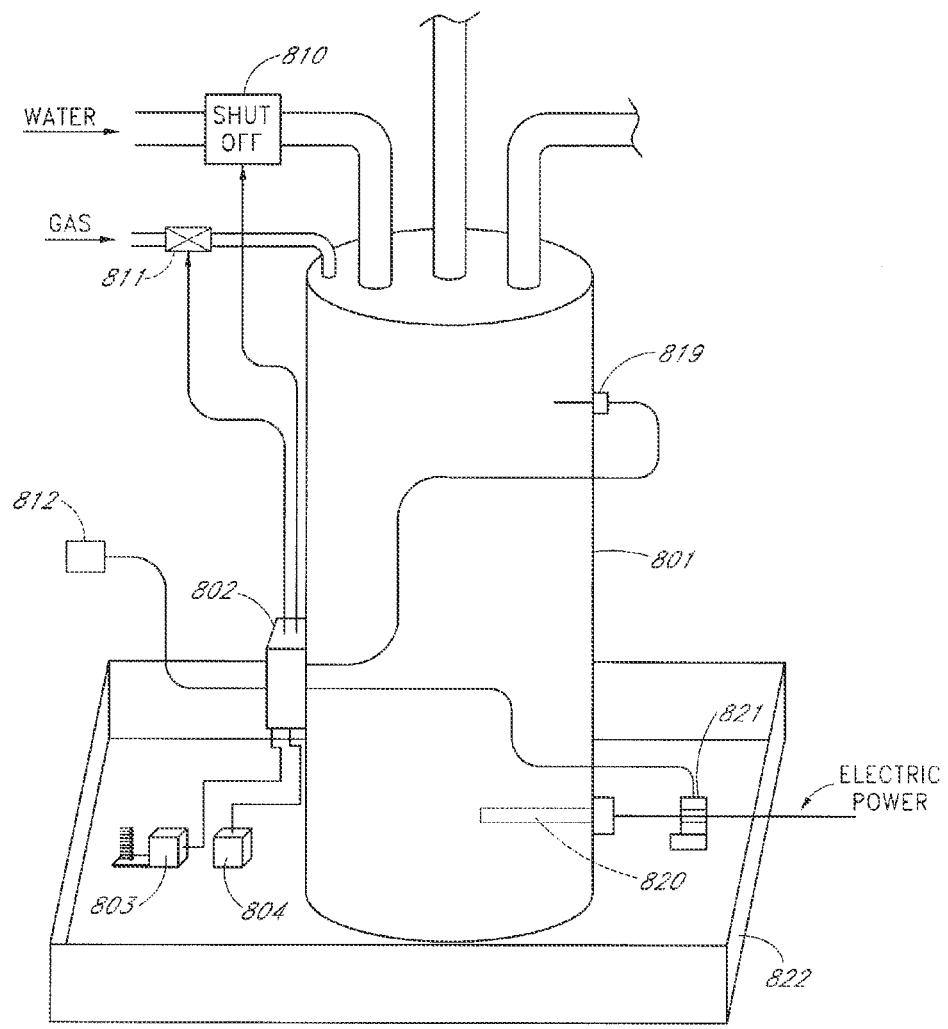
FIG. 8 shows how the sensor system can be used to detect water leaks.

FIG. 8 shows the sensor system used to detect water leaks. In one embodiment, the sensor unit 102 includes a water level sensor 803 and/or a water temperature sensor 804. The water level sensor 803 and/or water temperature sensor 804 are placed, for example, in a tray underneath a water heater 801 in order to detect leaks from the water heater 801 and thereby, prevent water damage from a leaking water heater. In one embodiment, an temperature sensor is also provided to measure temperature near the water heater. The water level sensor can also be placed under a sink, in a floor sump, etc. In one embodiment, the severity of a leak is ascertained by the sensor unit 102 (or the monitoring computer 113) by measuring the rate of rise in the water level. When placed near the hot water tank 801, the severity of a leak can also be ascertained at least in part by measuring the temperature of the water. In one embodiment, a first water flow sensor is placed in an input water line for the hot water tank 801 and a second water flow sensor is placed in an output water line for the hot water tank. Leaks in the tank can be detected by observing a difference between the water flowing through the two sensors.

In one embodiment, a remote shutoff valve 810 is provided, so that the monitoring system 100 can shutoff the water supply to the water heater when a leak is detected. In one embodiment, the shutoff valve is controlled by the sensor unit 102. In one embodiment, the sensor unit 102 receives instructions from the base unit 112 to shut off the water supply to the heater 801. In one embodiment, the responsible party 120 sends instructions to the monitoring computer 113 instructing the monitoring computer 113 to send water shut off instructions to the sensor unit 102. Similarly, in one embodiment, the sensor unit 102 controls a gas shutoff valve 811 to shut off the gas supply to the water heater 801 and/or to a furnace (not shown) when dangerous conditions (such as, for example, gas leaks, carbon monoxide, etc.) are detected. In one embodiment, a gas detector 812 is provided to the sensor unit 102. In one embodiment, the gas detector 812 measures carbon monoxide. In one embodiment, the gas detector 812 measures flammable gas, such as, for example, natural gas or propane.

In one embodiment, an optional temperature sensor 818 is provided to measure stack temperature. Using data from the temperature sensor 818, the sensor unit 102 reports conditions, such as, for example, excess stack temperature. Excess stack temperature is often indicative of poor heat transfer (and thus poor efficiency) in the water heater 818.

In one embodiment, an optional temperature sensor 819 is provided to measure temperature of water in the water heater 810. Using data from the temperature sensor 819, the sensor unit 102 reports conditions, such as, for example, over-temperature or under-temperature of the water in the water heater.

In one embodiment, an optional current probe 821 is provided to measure electric current provided to a heating element 820 in an electric water heater. Using data from the current probe 821, the sensor unit 102 reports conditions, such as, for example, no current (indicating a burned-out heating element 820). An over-current condition often indicates that the heating element 820 is encrusted with mineral deposits and needs to be replaced or cleaned. By measuring the current provided to the water heater, the monitoring system can measure the amount of energy provided to the water heater and thus the cost of hot water, and the efficiency of the water heater.

In one embodiment, the sensor 803 includes a moisture sensor. Using data from the moisture sensor, the sensor unit 102 reports moisture conditions, such as, for example, excess moisture that would indicate a water leak, excess condensation, etc.

In one embodiment, the sensor unit 102 is provided to a moisture sensor (such as the sensor 803) located near an air conditioning unit. Using data from the moisture sensor, the sensor unit 102 reports moisture conditions, such as, for example, excess moisture that would indicate a water leak, excess condensation, etc.

In one embodiment, the sensor 201 includes a moisture sensor. The moisture sensor can be placed under a sink or a toilet (to detect plumbing leaks) or in an attic space (to detect roof leaks).

Excess humidity in a structure can cause severe problems such as rotting, growth of molds, mildew, and fungus, etc. (hereinafter referred to generically as fungus). In one embodiment, the sensor 201 includes a humidity sensor. The humidity sensor can be placed under a sink, in an attic space, etc., to detect excess humidity (due to leaks, condensation, etc.). In one embodiment, the monitoring computer 113 compares humidity measurements taken from different sensor units in order to detect areas that have excess humidity. Thus, for example, the monitoring computer 113 can compare the humidity readings from a first sensor unit 102 in a first attic area, to a humidity reading from a second sensor unit 102 in a second area. For example, the monitoring computer can take humidity readings from a number of attic areas to establish a baseline humidity reading and then compare the specific humidity readings from various sensor units to determine if one or more of the units are measuring excess humidity. The monitoring computer 113 would flag areas of excess humidity for further investigation by maintenance personnel. In one embodiment, the monitoring computer 113 maintains a history of humidity readings for various sensor units and flags areas that show an unexpected increase in humidity for investigation by maintenance personnel.

In one embodiment, the monitoring system 100 detects conditions favorable for fungus (e.g., mold, mildew, fungus, etc.) growth by using a first humidity sensor located in a first building area to produce first humidity data and a second humidity sensor located in a second building area to produce second humidity data. The building areas can be, for example, areas near a sink drain, plumbing fixture, plumbing, attic areas, outer walls, a bilge area in a boat, etc.

The monitoring station 113 collects humidity readings from the first humidity sensor and the second humidity sensor and indicates conditions favorable for fungus growth by comparing the first humidity data and the second humidity data. In one embodiment, the monitoring station 113 establishes a baseline humidity by comparing humidity readings from a plurality of humidity sensors and indicates possible fungus growth conditions in the first building area when at least a portion of the first humidity data exceeds the baseline humidity by a specified amount. In one embodiment, the monitoring station 113 establishes a baseline humidity by comparing humidity readings from a plurality of humidity sensors and indicates possible fungus growth conditions in the first building area when at least a portion of the first humidity data exceeds the baseline humidity by a specified percentage.

In one embodiment, the monitoring station 113 establishes a baseline humidity history by comparing humidity readings from a plurality of humidity sensors and indicates possible fungus growth conditions in the first building area when at least a portion of the first humidity data exceeds the baseline humidity history by a specified amount over a specified period of time. In one embodiment, the monitoring station 113 establishes a baseline humidity history by comparing humidity readings from a plurality of humidity sensors over a period of time and indicates possible fungus growth conditions in the first building area when at least a portion of the first humidity data exceeds the baseline humidity by a specified percentage of a specified period of time.

In one embodiment, the sensor unit 102 transmits humidity data when it determines that the humidity data fails a threshold test. In one embodiment, the humidity threshold for the threshold test is provided to the sensor unit 102 by the monitoring station 113. In one embodiment, the humidity threshold for the threshold test is computed by the monitoring station from a baseline humidity established in the monitoring station. In one embodiment, the baseline humidity is computed at least in part as an average of humidity readings from a number of humidity sensors. In one embodiment, the baseline humidity is computed at least in part as a time average of humidity readings from a number of humidity sensors. In one embodiment, the baseline humidity is computed at least in part as a time average of humidity readings from a humidity sensor. In one embodiment, the baseline humidity is computed at least in part as the lesser of a maximum humidity reading an average of a number of humidity readings.

In one embodiment, the sensor unit 102 reports humidity readings in response to a query by the monitoring station 113. In one embodiment, the sensor unit 102 reports humidity readings at regular intervals. In one embodiment, a humidity interval is provided to the sensor unit 102 by the monitoring station 113.

In one embodiment, the calculation of conditions for fungus growth is comparing humidity readings from one or more humidity sensors to the baseline (or reference) humidity. In one embodiment, the comparison is based on comparing the humidity readings to a percentage (e.g., typically a percentage greater than 100%) of the baseline value. In one embodiment, the comparison is based on comparing the humidity readings to a specified delta value above the reference humidity. In one embodiment, the calculation of likelihood of conditions for fungus growth is based on a time history of humidity readings, such that the longer the favorable conditions exist, the greater the likelihood of fungus growth. In one embodiment, relatively high humidity readings over a period of time indicate a higher likelihood of fungus growth than relatively high humidity readings for short periods of time. In one embodiment, a relatively sudden increase in humidity as compared to a baseline or reference humidity is reported by the monitoring station 113 as a possibility of a water leak. If the relatively high humidity reading continues over time then the relatively high humidity is reported by the monitoring station 113 as possibly being a water leak and/or an area likely to have fungus growth or water damage.

Temperatures relatively more favorable to fungus growth increase the likelihood of fungus growth. In one embodiment, temperature measurements from the building areas are also used in the fungus grown-likelihood calculations. In one embodiment, a threshold value for likelihood of fungus growth is computed at least in part as a function of temperature, such that temperatures relatively more favorable to fungus growth result in a relatively lower threshold than temperatures relatively less favorable for fungus growth. In one embodiment, the calculation of a likelihood of fungus growth depends at least in part on temperature such that temperatures relatively more favorable to fungus growth indicate a relatively higher likelihood of fungus growth than temperatures relatively less favorable for fungus growth. Thus, in one embodiment, a maximum humidity and/or minimum threshold above a reference humidity is relatively lower for temperature more favorable to fungus growth than the maximum humidity and/or minimum threshold above a reference humidity for temperatures relatively less favorable to fungus growth.

In one embodiment, a water flow sensor is provided to the sensor unit 102. The sensor unit 102 obtains water flow data from the water flow sensor and provides the water flow data to the monitoring computer 113. The monitoring computer 113 can then calculate water usage. Additionally, the monitoring computer can watch for water leaks, by, for example, looking for water flow when there should be little or no flow. Thus, for example, if the monitoring computer detects water usage throughout the night, the monitoring computer can raise an alert indicating that a possible water leak has occurred.

In one embodiment, the sensor 201 includes a water flow sensor provided to the sensor unit 102. The sensor unit 102 obtains water flow data from the water flow sensor and provides the water flow data to the monitoring computer 113. The monitoring computer 113 can then calculate water usage. Additionally, the monitoring computer can watch for water leaks, by, for example, looking for water flow when there should be little or no flow. Thus, for example, if the monitoring computer detects water usage throughout the night, the monitoring computer can raise an alert indicating that a possible water leak has occurred.

In one embodiment, the sensor 201 includes a fire-extinguisher tamper sensor provided to the sensor unit 102. The fire-extinguisher tamper sensor reports tampering with or use of a fire-extinguisher. In one embodiment the fire-extinguisher tamper sensor reports that the fire extinguisher has been removed from its mounting, that a fire extinguisher compartment has been opened, and/or that a safety lock on the fire extinguisher has been removed.

In one embodiment, the sensor unit 102 is configured as an adjustable-threshold sensor that computes a reporting threshold level. In one embodiment, the reporting threshold is computed as an average of a number of sensor measurements. In one embodiment, the average value is a relatively long-term average. In one embodiment, the average is a time-weighted average wherein recent sensor readings used in the averaging process are weighted differently than less recent sensor readings. In one embodiment, more recent sensor readings are weighted relatively more heavily than less recent sensor readings. In one embodiment, more recent sensor readings are weighted relatively less heavily than less recent sensor readings. The average is used to set the reporting threshold level. When the sensor readings rise above the reporting threshold level, the sensor indicates a notice condition. In one embodiment, the sensor indicates a notice condition when the sensor reading rises above the reporting threshold value for a specified period of time. In one embodiment, the sensor indicates a notice condition when a statistical number of sensor readings (e.g., 3 of 2, 5 of 3, 10 of 7, etc.) are above the reporting threshold level. In one embodiment, the sensor unit 102 indicates various levels of alarm (e.g., warning, alert, alarm) based on how far above the reporting threshold the sensor reading has risen.

In one embodiment, the sensor unit 102 computes the notice level according to how far the sensor readings have risen above the threshold and how rapidly the sensor readings have risen. For example, for purposes of explanation, the level of readings and the rate of rise can be quantified as low, medium, and high. The combination of sensor reading level and rate of rise then can be shown as a table, as shown in Table 1. Table 1 provides examples and is provided by way of explanation, not limitation.

TABLE 1

| | Sensor Reading Level (as compared to the reporting threshold) | | | |
|---|---|---|---|---|
| Rate of Rise | High | Warning | Alarm | Alarm |
| | Medium | Notice | Warning | Alarm |
| | Low | Notice | Warning | Alarm |
| | | Low | Medium | High |

One of ordinary skill in the art will recognize that the notice level N can be expressed as an equation $N=f(t, v, r)$, where $t$ is the reporting threshold level, $v$ is the sensor reading, and $r$ is the rate of rise of the sensor reading. In one embodiment, the sensor reading $v$ and/or the rate of rise $r$ are lowpass filtered in order to reduce the effects of noise in the sensor readings. In one embodiment, the reporting threshold is computed by lowpass filtering the sensor readings $v$ using a filter with a relatively low cutoff frequency. A filter with a relatively low cutoff frequency produces a relatively long-term averaging effect. In one embodiment, separate reporting thresholds are computed for the sensor reading and for the rate of rise.

In one embodiment, a calibration procedure period is provided when the sensor unit 102 is powered up. During the calibration period, the sensor data values from the sensor 201 are used to compute one or more thresholds, but the sensor does not compute notices, warnings, alarms, etc., until the calibration period is complete. In one embodiment, the sensor unit 102 uses a fixed (e.g., pre-programmed) threshold value to compute notices, warnings, and alarms during the calibration period and then uses the adjustable reporting threshold value once the calibration period has ended.

In one embodiment, the sensor unit 102 determines that a failure of the sensor 201 has occurred when the adjustable reporting threshold value exceeds a maximum adjustable threshold value. In one embodiment, the sensor unit 102 determines that a failure of the sensor 201 has occurred when the adjustable threshold value falls below a minimum adjustable threshold value. The sensor unit 102 can report such failure of the sensor 201 to the base unit 112.

In one embodiment, the sensor unit 102 obtains a number of sensor data readings from the sensor 201 and computes one or more calibration and/or reporting thresholds as a weighted average using a weight vector. The weight vector weighs some sensor data readings relatively more than other sensor data readings.

In one embodiment, the sensor unit 102 obtains a number of sensor data readings from the sensor unit 201 and filters the sensor data readings and calculates the threshold value from the filtered sensor data readings. In one embodiment, the sensor unit applies a lowpass filter. In one embodiment, the sensor unit 201 uses a Kalman filter to remove unwanted components from the sensor data readings. In one embodiment, the sensor unit 201 discards sensor data readings that are "outliers" (e.g., too far above or too far below a normative value). In this manner, the sensor unit 102 can compute the threshold value even in the presence of noisy sensor data.

In one embodiment, the sensor unit 102 indicates a notice condition (e.g., alert, warning, alarm) when the reporting threshold value changes too rapidly. In one embodiment, the sensor unit 102 indicates a notice condition (e.g., alert, warning, alarm) when the threshold value exceeds a specified maximum value. In one embodiment, the sensor unit 102 indicates a notice condition (e.g., alert, warning, alarm) when the threshold value falls below a specified minimum value.

In one embodiment, the sensor unit 102 adjusts one or more operating parameters of the sensor 201 according to one or more threshold values. Thus, for example, in the example of an optical smoke sensor, the sensor unit 201 can reduce the power used to drive the LED in the optical smoke sensor when the threshold value indicates that the optical smoke sensor can be operated at lower power (e.g., low ambient light conditions, clean sensor, low air particulate conditions, etc.). The sensor unit 201 can increase the power used to drive the LED when the threshold value indicates that the optical smoke sensor should be operated at higher power (e.g., high ambient light, dirty sensor, higher particulates in the air, etc.).

In one embodiment, an output from a Heat Ventilating and/or Air Conditioning (HVAC) system 350 is optionally provided to the sensor unit 102 as shown in FIG. 2. In one embodiment, an output from the HVAC system 350 is optionally provided to the repeater 110 as shown in FIG. 3 and/or to the monitoring system 113 as shown in FIG. 4. In this manner, the system 100 is made aware of the operation of the HVAC system. When the HVAC system turns on or off, the airflow patterns in the room change, and thus, the way in which smoke or other materials (e.g., flammable gases, toxic gases, etc.) changes as well. Thus, in one embodiment, the threshold calculation takes into account the airflow effects caused by the HVAC system. In one embodiment, an adaptive algorithm is used to allow the sensor unit 102 (or monitoring system 113) to "learn" how the HVAC system affects sensor readings and thus, the sensor unit 102 (or monitoring system 113) can adjust the threshold level accordingly. In one embodiment, the threshold level is temporarily changed for a period of time (e.g., raised or lowered) to avoid false alarms when the HVAC system turns on or off. Once the airflow patterns in the room have re-adjusted to the HVAC state, then the threshold level can be re-established for desired system sensitivity.

Thus, for example, in one embodiment where an averaging or lowpass filter type process is used to establish the threshold level, the threshold level is temporarily set to de-sensitize the sensor unit 102 when the HVAC system turns on or off, thus allowing the averaging or lowpass filtering process to establish a new threshold level. Once a new threshold level is established (or after a specified period of time), then the sensor unit 102 returns to its normal sensitivity based on the new threshold level.

In one embodiment, the sensor 201 is configured as an infrared sensor. In one embodiment, the sensor 201 is configured as an infrared sensor to measure a temperature of objects within a field of view of the sensor 201. In one embodiment, the sensor 201 is configured as an infrared sensor. In one embodiment, the sensor 201 is configured as an infrared sensor to detect flames within a field of view of the sensor 201. In one embodiment, the sensor 201 is configured as an infrared sensor.

In one embodiment, the sensor 201 is configured as an imaging sensor. In one embodiment, the controller 202 is configured to detect flames by processing of image data from the imaging sensor.

Figure 9:
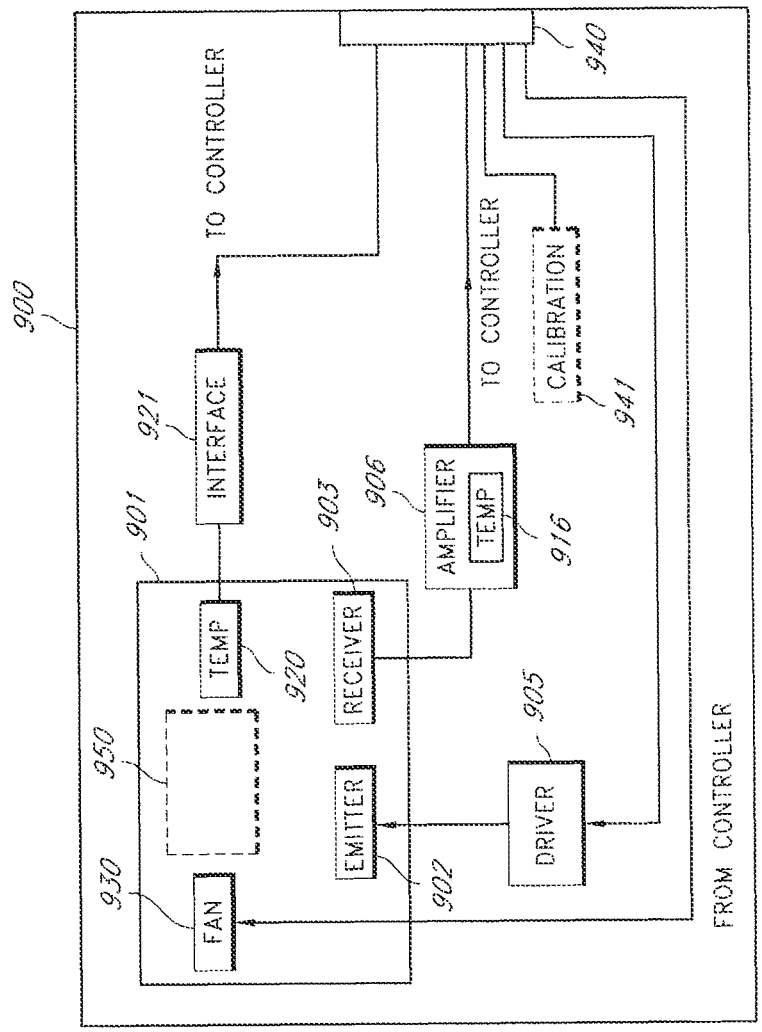
FIG. 9 shows an optical smoke sensor configured to operate at a relatively high sensitivity.

FIG. 9 shows an optical smoke sensor 900 configured to operate at a relatively high sensitivity. The smoke sensor 900 is one embodiment of the sensor 201. The smoke sensor 900 includes a chamber 901, an emitter 902 provided to the chamber 901, and a photo-sensor 903 provided to the chamber 901. The emitter 902 and photo-sensor 903 are configured to sense smoke in a region 950 of the smoke chamber 901. In one embodiment, an optional temperature sensor 920 is also provided to the chamber 901. A driver 905 is provided to the emitter 902. The photo-sensor 903 is provided to an amplifier 906. In one embodiment, the emitter 902 emits infrared light and the photo-sensor 903 senses infrared light. In one embodiment, the emitter 902 emits visible light and the photo-sensor 903 senses visible light. In one embodiment, the emitter 902 is configured as a plurality of emitters and/or a multi-spectrum emitter configured to emit light in a plurality of wavelengths (e.g., infrared light, red light, green light, blue light, ultraviolet light, etc.) and the photo-sensor 903 is configured as a plurality of photo-sensors and/or multi-spectral sensors to sense the plurality of wavelengths emitted by the emitter 902. In one embodiment, the photo-sensor 903 is configured to sense light in a band or bands corresponding to light emitted by the emitter 902 and to reject light in other bands. In one embodiment, the photo-sensor 903 is configured to sense light in a selected wavelength band corresponding to light emitted by the emitter 902 and to reject light in other bands. In one embodiment one or more filters are provided to the photo-sensor 903 to make the photo-sensor 903 relatively insensitive to light in undesired wavelengths.

The optional temperature sensor 920 is provided to an interface 921. In one embodiment, an optional fan 930 is provided to the smoke chamber 901. The fan 930 can be provided within the smoke chamber 901 and/or the fan 930 can be provided external to the smoke chamber 901. The fan 930 is configured to increase airflow and air exchange between the smoke chamber 901 and the region outside the smoke chamber 901. The fan 930 can be conventional rotary fan, a piezoelectric fan, etc.

In one embodiment, an optional calibration module 941 is provided by the sensor 900 to the controller 202. As described in more detail below, the calibration module 941 can provide calibration data for the sensor unit 900 and/or software for the sensor unit 900.

In operation, the driver 905 generates one or more drive pulses in response to commands from the controller 202. The drive pulses are provided to the emitter 902 which generates optical radiation in the chamber 901. The photo-sensor 903 senses the optical radiation from the emitter 902 (e.g., as radiation scattered by the chamber, radiation scattered by smoke in the chamber, etc.). The amplifier 906 amplifies signals from the photo-sensor 903 and provides the sensor data to the controller 202. In one embodiment, the amplifier 906 includes one or more temperature sensors 916 that provides temperature compensation to correct temperature variations of the photo-sensor 903. The temperature compensation of the amplifier 906 at least partially stabilizes the signals from the photo-sensor 903 and thus, allows the sensor 900 to be operated at relatively higher sensitivity while reducing the number of temperature-created false alarms.

Figure 10:
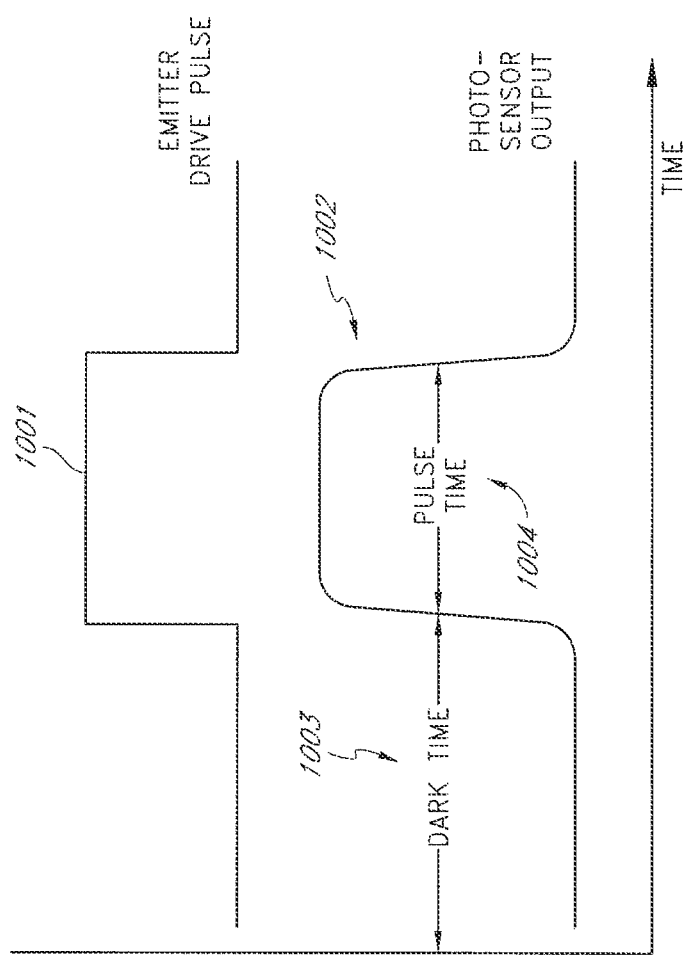
FIG. 10 shows a emitter drive pulse and photo-sensor outputs during dark time and during pulse time.

FIG. 10 shows an emitter drive pulse 1001 and photo-sensor output 1002 during dark time 1003 and during pulse time 1004 (when the emitter drive pulse is driving the emitter 902). The sensor unit 900 can be calibrated at least in part by collecting data from the photo-sensor 903 during the dark time 1003 and during the pulse time 1004. During the dark time 1003, the emitter 902 is producing little or no radiation, and thus, the signals produced by the photo-sensor 903 are not due to radiation emitted by the emitter 902, but rather are produced by ambient light and/or by the photo-sensor 902 itself (e.g., thermal noise, radio interference, etc.). Thus, the signals produced by the photo-sensor 903 during the dark time 1003 can be used to establish a first background level or first reference level for the sensor 900. A second reference level can be established by measuring the output of the photo-sensor 903 during the pulse time 1004 when smoke is not present (or not expected to be present). In a scattering sensor, the photo-sensor 903 does not directly receive radiation from the emitter 902, but rather receives radiation from the emitter 902 that is scattered by smoke, water vapor, the chamber 901, etc. When no smoke, water vapor, and the like is present, then the difference between the first reference level and the second reference level is due to scattering from the chamber 901. If the second reference level is relatively higher than the first reference level, then the controller 202 knows that the emitter 902 and photo-sensor 903 are operating and that the emitter is producing enough radiation to overcome the ambient light and other background noise. If the second reference level does not rise above the first reference level, the controller can, in one embodiment, instruct the driver 905 to increase the drive pulse and thus, produce more radiation from the emitter 902. If the second reference level is not higher than the first reference level (e.g., during operation or, if provided, after increasing the drive pulse), then the controller 202 can send a fault message to the base unit 113 indicating that a fault has occurred in the sensor 900. If no fault is detected, then the smoke measurements are obtained by comparing sensor measure data with second reference level. Smoke is detected when the measured data from the sensor exceeds the second reference level by a specified amount.

Figure 11:
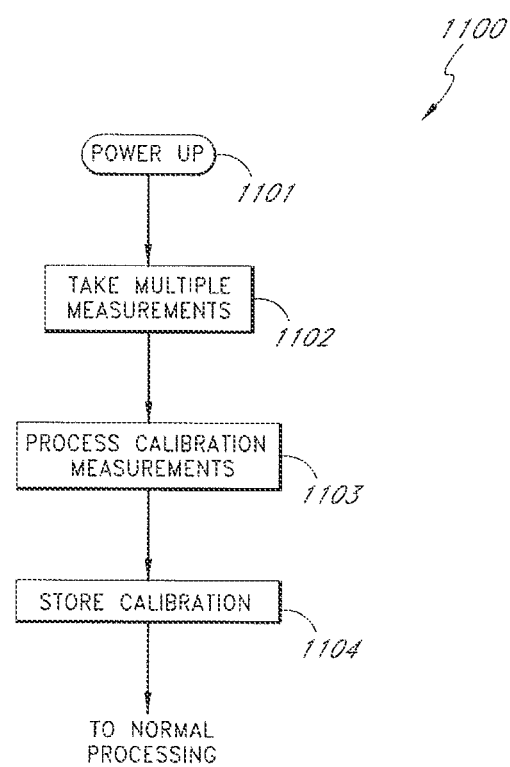
FIG. 11 shows a calibration sequence for the optical smoke sensor of FIG. 9.

FIG. 11 shows a calibration sequence 1100 for the optical smoke sensor of FIG. 9. At power-up 1101, it is assumed that there is no smoke present and the controller 202 takes one or more calibration measurements using the sensor 900. A first set of calibration measurements is taken during the dark period 1003. A second set of calibration measurements is taken during the pulse period 1004. In one embodiment, the largest measurement during the pulse period 1004 is used as the second reference level. In one embodiment, an average of several of the relatively largest measurements during the pulse period 1004 is used as the second reference level.

The optional fan 930 can advantageously be used to increase air/smoke exchange between the chamber 901 and the air/smoke in the room. In one embodiment, the fan 930 is controlled by the controller 202 such that the controller 202 determines when, and if, the fan 930 is operated. Since operation of the fan 930 may reduce battery life, in one embodiment, the controller 202 operates the fan 930 on an intermittent basis in connection with smoke measurements. In one embodiment, the controller operates the fan during smoke measurements. In one embodiment, the controller operates the fan between smoke measurements (e.g., between pulses of radiation from the emitter 902) and does not operate the fan during smoke measurements. In one embodiment, when a smoke measurement indicates that there may be smoke present, the controller 202 operates the fan 930 for a relatively brief period (to try and draw additional smoke into the chamber 901) and then takes additional smoke measurements. The fan increases air exchange with the smoke chamber 901 and thus, makes the smoke sensor 900 respond relatively more quickly to changes in the level of smoke near the sensor 900. Thus, for example, in some configurations, smoke may become temporarily trapped in the smoke chamber 901 and cause the sensor 900 to report the presence of smoke even after smoke in the room has dissipated. By using the fan, the controller 202 can cause relatively more air exchange of the smoke chamber, clear trapped smoke from the chamber 901, and thereby cause the sensor 900 to respond relatively more rapidly to changes in the ambient smoke level.

In one embodiment, the controller 202 operates the fan in response to one or more commands from the computer 113. Thus, for example, if the computer 113 receives smoke measurements from the sensor unit 103, which is located relatively near the sensor unit 102 (e.g., in the same apartment, same hallway, same portion of a building, etc.) then the computer 113 can instruct the controller 202 in the sensor unit 102 to activate the fan 930 in order to improve the response time of the sensor unit 102. In one embodiment, the computer 113 instructs the sensor unit 102 to first take one or more smoke sensor measurements (without activating the fan 930) and report these first measurements back to the computer 113. The computer 113 can then instruct the controller 202 to active the fan 930 and then take one or more smoke sensor measurements (with the fan 930 running/and or after the fan 930 has been stopped) and report the second smoke sensor measurements. If either the first or second set of smoke sensor measurements indicates smoke is present, then the computer 113 can report that the area affected by smoke includes the area proximate to both the sensor units 102 and 103.

In one embodiment, the controller 202 stores three threshold levels. The first threshold level corresponds to one or more first measurements taken by the photo-sensor 903 when the emitter 902 is not operating. Thus, the first threshold corresponds generally to the dark current of the photo-sensor 903 and ambient light detected by the photo-sensor 903. In one embodiment, the first threshold is computed by selecting the maximum of the first measurements. In one embodiment, the first threshold is computed by averaging one or more of the first measurements. The resulting first threshold is then stored. In one embodiment, the ambient temperature present at the time of the first measurements is recorded. A correction factor can be applied to the first threshold to account for ambient temperature. In one embodiment, the temperature correction is provided by analog circuitry associated with the photo-sensor 903 (e.g., by thermistors 916 used to compensate the gain characteristics of the amplifier 906). In one embodiment, the temperature correction is computed digitally by the controller 202 using data from the temperature sensor 920. In one embodiment, both analog compensation using the temperature sensors 916, and digital compensation using data from the temperature sensor 920 are used. The resulting first threshold is then stored.

The first threshold can vary according to the temperature of the photo-sensor 903 and the presence or absence of ambient light. Thus, when taking actual smoke measurements or running diagnostics, the controller 202 can re-measure the output of the photo-sensor 903 when the emitter 902 is not operating, re-compute the first threshold, and compare the re-computed first threshold value with the stored first threshold value. If the re-computed first threshold value differs from the stored first threshold value by a specified error threshold, then the controller 202 can report to the monitoring computer 113 that an anomalous condition or fault condition has occurred.

The second threshold corresponds to one or more second measurements taken by the photo-sensor 903 when the emitter 902 is pulsed, but when smoke is not expected to be present. Thus in a scattering-type smoke sensor, the second threshold corresponds generally to the light detected by the photo-sensor 903 that is scattered by the chamber 901. In an obscuration-type smoke sensor, the second threshold corresponds generally to the light detected by the photo-sensor 903 from the emitter 902. In one embodiment, the second threshold is computed by selecting the maximum of the second measurements. In one embodiment, the second threshold is computed by averaging one or more of the second measurements. In one embodiment, the ambient temperature present at the time of the second measurements is recorded. A correction factor can be applied to the second threshold to account for ambient temperature. In one embodiment, the temperature correction is provided by analog circuitry associated with the photo-sensor 903 (e.g., by thermistors 916 used to compensate the gain characteristics of the amplifier 906). In one embodiment, the temperature correction is computed digitally by the controller 202 using data from the temperature sensor 920. In one embodiment, both analog compensation using the temperature sensors 916, and digital compensation using data from the temperature sensor 920 are used.

The resulting second threshold is then stored. Thus, when running diagnostics, the controller 202 can re-measure the output of the photo-sensor 903 when the emitter 902 is operating, re-compute the second threshold, and compare the re-computed second threshold value with the stored second threshold value. If the re-computed second threshold value differs from the stored second threshold value by a specified error threshold, then the controller 202 can report to the monitoring computer 113 that an anomalous condition or fault condition has occurred. Typically, the second threshold will be relatively larger than the first threshold. Thus, in one embodiment, the controller 202 can compare the first threshold with the second threshold. If the second threshold is not relatively larger than the first threshold, then an anomalous condition or error condition can be reported.

The third threshold corresponds to the reporting threshold described above, and is the threshold level at which the controller determines that smoke may be present and that the sensor measurements should be reported to the monitoring computer 113. In one embodiment, the controller 202 computes the third threshold as a function of the second threshold (e.g., as a percentage increase, as a fixed increase, etc.). In one embodiment, the controller 202 computes the third threshold as a function of the first threshold and the second threshold. In one embodiment, the controller 202 reports the second threshold (and, optionally the first threshold) to the monitoring computer 113, and the monitoring computer computes the desired third threshold and sends the third threshold to the controller 202. As described in connection with FIG. 6, if the measured data from the photo sensor 903 exceeds the third threshold (the reporting threshold) then the controller 202 sends the measured smoke data to the monitoring computer 113. Moreover, as described above, the value of the third threshold (the reporting threshold) is adjustable and can be lowered relatively closer to the second threshold to increase the sensitivity of the sensor unit 102.

The sensitivity of the sensor unit 102 increases as the third threshold (the reporting threshold) approaches the second threshold, and the sensitivity of the sensor unit 102 decreases as the third threshold increased above the second threshold. Moreover, the sensitivity of the sensor unit 102 increases as the second threshold decreases. Although the second threshold should typically not be lower than the first threshold, the value of the first threshold can vary due to the temperature of the photo-sensor 903 and the ambient light. Thus, in one embodiment, the controller periodically re-measures the first and second thresholds and re-computes the third threshold to provide relatively high sensitivity as allowed by current conditions.

In one embodiment, the controller computes both the second and third threshold values based on the measured first threshold value. Since the first threshold value is measured when the emitter is 902 is not operating, the first threshold value is relatively independent of the presence of smoke and depends primarily on the ambient temperature and the presence of ambient light. Thus, the controller can re-measure the first threshold and compute the second threshold using the stored first and second threshold values obtained during calibration.

In one embodiment, the smoke sensor 900 is configured as a replaceable module. A connector 940 is provided to the smoke sensor 900 to allow the smoke sensor 900 to be provided to the controller 202. In one embodiment, the smoke sensor 900 is calibrated (e.g., calibrated at the factory, calibrated before installation, calibrated during installation, etc.) and the calibration data is provided to a calibration module 941. The calibration module 941 provides the calibration data to the controller 202 so that the controller 202 knows the characteristics of the smoke sensor 900. In one embodiment, the calibration module 941 is configured as a read-only memory (ROM) that provides calibration data.

In one embodiment, the calibration module 941 is configured as a ROM that provides software used by the controller 202 to, at least in part, operate the sensor 900. By providing software with the sensor module 900, different types of sensor modules, upgraded sensor modules, etc., can be plugged into the sensor unit 102 for use by the controller 202. In one embodiment, flash memory is provided (in the calibration module 941 and/or in the controller 202) to allow the monitoring computer 113 or installation personal to download new software into the sensor unit 102.

In one embodiment, calibration data provided by the calibration module 941 includes expected ranges for the first threshold and/or the second threshold. The controller 202 can report a fault if the actual first and/or second threshold values measured (or computed) by the controller 202 fall outside the ranges specified by the calibration module 941.

Figure 12:
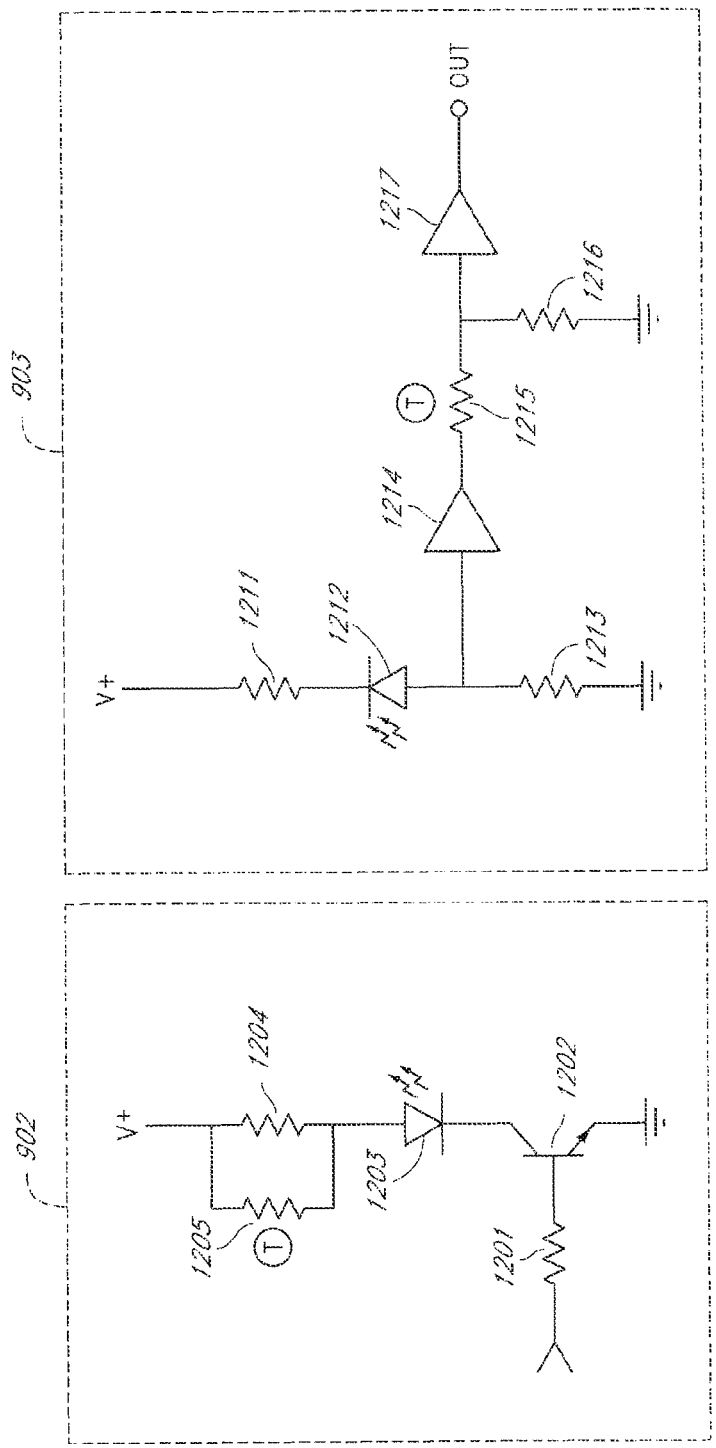
FIG. 12 shows one embodiment of temperature compensation in an optical smoke detector.

FIG. 12 shows one embodiment of temperature compensation for the emitter 902 and the photo-detector 903. In the embodiment of FIG. 12, an input to the emitter 902 is provided through a resistor 1201 to a control input of a transistor 1202 (the transistor 1202 is shown as an NPN transistor, but one of skill in the art will recognize the transistor 1202 can also be configured as a PNP transistor, FET transistor, MOSFET transistor, etc.). The transistor 1202 is configured such that when the transistor 1202 is in a conducting state, the transistor 1202 provides current from a photo-emitter diode 1203 to ground. Current from a V+supply is provided to the diode 1203 by a parallel combination of a resistor 1204 and a thermistor 1205. In one embodiment, the thermistor 1205 has a negative temperature coefficient. In one embodiment, the resistance of the resistor 1204 is relatively smaller than the resistance of the thermistor 1205. In one embodiment, the resistance of the resistor 1204 is substantially smaller than the resistance of the thermistor 1205.

In the embodiment of FIG. 12, in photo-detector 903, the V+supply is provided through a resistor 1211 to a reverse-biased photo-detector diode 1212. The photo-diode 1212 is provided to ground through a resistor 1213. The ungrounded terminal of the resistor 1213 is also provided to an input of an amplifier 1214. An output of the amplifier 1214 is provided to ground through a thermistor 1215 to an input of an amplifier 1217. The input of the amplifier 1217 is also provided to ground through a resistor 1216, such that the thermistor 1215 and the resistor 1216 form a voltage divider. In one embodiment, the thermistor 1215 has a negative temperature coefficient. An output of the amplifier 1217 is provided as an output of the photo-detector 903.

The thermistor 1205 provides temperature compensation for the photo-emitter diode 1203 to stabilize the operation of the diode 1203 with respect to temperature. The thermistor 1215 provides temperature compensation for the photo-detector diode 1203 to stabilize the operation of the diode 1212 with respect to temperature. Thus, the embodiments of the emitter 902 and photo-detector 903 shown in FIG. 12 provide an output that is relatively more stable with temperature changes than embodiments that are not temperature corrected. The use of temperature correction shown in FIG. 12 allows the sensor unit 102 to operate at relatively higher sensitivity without producing excess false alarms.

Use of one or more, or combined use of two or more, of the techniques disclosed above, (e.g., variable threshold, temperature compensation, multi-threshold calibration, tend analysis, fans, etc.) allows the sensor unit 102 to operate relatively reliably at relatively higher sensitivities than prior art sensor units. The ability to operate relatively reliably at higher sensitivities (e.g., to detect smoke at lower concentrations without generating an unacceptable number of false alarms) allows the system 100 to detect fires or other dangerous conditions more quickly and with greater accuracy than prior art systems.

It will be evident to those skilled in the art that the invention is not limited to the details of the foregoing illustrated embodiments and that the present invention may be embodied in other specific forms without departing from the spirit or essential attributed thereof; furthermore, various omissions, substitutions and changes may be made without departing from the spirit of the invention. For example, although specific embodiments are described in terms of the 900 MHz frequency band, one of ordinary skill in the art will recognize that frequency bands above and below 900 MHz can be used as well. The wireless system can be configured to operate on one or more frequency bands, such as, for example, the HF band, the VHF band, the UHF band, the Microwave band, the Millimeter wave band, etc. One of ordinary skill in the art will further recognize that techniques other than spread spectrum can also be used. The modulation is not limited to any particular modulation method, such that modulation scheme used can be, for example, frequency modulation, phase modulation, amplitude modulation, combinations thereof, etc. The foregoing description of the embodiments is, therefore, to be considered in all respects as illustrative and not restrictive, with the scope of the invention being delineated by the appended claims and their equivalents.

What is claimed is:

1. A wireless device comprising:
    a smoke sensor configured to obtain measurement data regarding a level of smoke;
    a wireless transceiver capable of wirelessly transmitting and receiving information to and from an electronic device located remotely from the wireless device;
    a power source for powering operation of the wireless device; and
    a controller operatively coupled to the wireless transceiver and the smoke sensor and configured to:
        operate the wireless device in a sleep mode whereby consumption of power from the power source is lower than when the wireless device operates in an awake mode;
        temporarily switch the wireless device from the sleep mode to the awake mode;
        operate the smoke sensor to obtain first measurement data regarding the level of smoke;
        operate the smoke sensor to obtain second measurement data regarding the level of smoke after obtaining the first measurement data; and
        adjust, based at least in part on the first measurement data:
            a reporting threshold level indicative of an amount of smoke deemed hazardous, and/or
            a rate at which the second measurement data is obtained, wherein the rate at which the second measurement data is obtained is different than a rate at which the first measurement data was obtained.

2. The wireless device of claim 1, wherein the wireless transceiver is configured to transmit and/or receive information and the smoke sensor is configured to obtain the second measurement data regarding the level of smoke while the wireless device is operating in the awake mode.

3. The wireless device of claim 1, wherein the wireless transceiver is inoperable to transmit or receive information when the wireless device is in the sleep mode.

4. The wireless device of claim 2, wherein the controller is configured to operate the wireless device in the sleep mode while obtaining the first measurement data and operate the wireless device in the awake mode while obtaining the second measurement data, the rate at which the second measurement data is obtained being higher than the rate at which the first measurement data is obtained.

5. The wireless device of claim 4, wherein the controller is configured to temporarily switch the wireless device from the sleep mode to the awake mode periodically.

6. The wireless device of claim 4, wherein the controller is configured to temporarily switch the wireless device from the sleep mode to the awake mode if a measured level of smoke of the first measurement data exceeds a predetermined threshold level.

7. The wireless device of claim 1, further including a tamper sensor; wherein the controller is further configured to cause the wireless device to switch from the sleep mode to the awake mode in response to receiving an indication of a fault condition from the tamper sensor when the wireless device from the sleep mode.

8. A method of operating a wireless device, comprising:
    operating the wireless device in a sleep mode, whereby consumption of power of the wireless device is lower than when the wireless device operates in an awake mode;
    temporarily causing the wireless device to switch from the sleep mode to the awake mode;
    obtaining, with a smoke sensor of the wireless device, first measurement data regarding a level of smoke;
    obtaining, with the smoke sensor, second measurement data regarding the level of smoke after obtaining the first measurement data; and
    adjusting, based at least in part on the first measurement data:
        a reporting threshold level indicative of an amount of smoke deemed hazardous, and/or
        a rate at which the second measurement data is obtained, wherein the rate at which the second measurement data is obtained is different than a rate at which the first measurement data was obtained.

9. The method of operating a wireless device of claim 8, wherein adjusting the reporting threshold level is based on a rate of increase of the level of smoke as indicated by the first measurement data.

10. The method of operating a wireless device of claim 8, wherein adjusting the reporting threshold level is based on an ambient temperature.

11. The method of operating a wireless device of claim 8, further comprising performing a diagnostic test of the wireless device and communicating information indicative of results of the diagnostic test to an electronic device located remotely from the wireless device via a wireless transceiver included in the wireless device.

12. The method of operating a wireless device of claim 8, further comprising:
    determining, based on the second measurement data, that the level of smoke exceeds the reporting threshold level; and
    communicating information indicating that the reporting threshold level has been exceeded to an electronic device located remotely from the wireless device via a wireless transceiver included in the wireless device.

13. The method of operating a wireless device of claim 11, wherein communicating the information occurs while the wireless device is in the awake mode, the method further comprising listening for instructions while in the awake mode, after communicating the reporting threshold level has been exceeded, and before returning back to the sleep mode.

14. The method of operating a wireless device of claim 8, further comprising:
wirelessly communicating information indicative of the first measurement data and/or the second measurement data from the wireless device to an electronic device located remote from the wireless device via a wireless transceiver included in the wireless device.

15. The method of operating a wireless device of claim 8, further comprising receiving, by the wireless device and during a reset interval, an identifier for the wireless device.

16. The method of operating a wireless device of claim 15, wherein the identifier is received via wireless communication.

17. A system for smoke detection, comprising:
means for operating a wireless device in a sleep mode, whereby consumption of power of the wireless device is lower than when the wireless device operates in an awake mode;
means for temporarily causing the wireless device to switch from the sleep mode to the awake mode;
means for obtaining first measurement data regarding a level of smoke and second measurement data regarding the level of smoke after obtaining the first measurement data; and
means for adjusting, based at least in part on the first measurement data:
a reporting threshold level indicative of an amount of smoke deemed hazardous, and/or
a rate at which the second measurement data is obtained, wherein the rate at which the second measurement data is obtained is different than a rate at which the first measurement data was obtained.

18. The system for smoke detection of claim 17, further comprising means for causing the wireless device to listen for one or more instructions while operating in the awake mode, and, in response to receiving the one or more instructions, perform one or more functions requested by the one or more instructions while operating in the awake mode.

19. The system for smoke detection of claim 17, further comprising:
means for determining an available radio frequency channel; and
means for wirelessly communicating information indicative of the level of smoke,
wherein the information indicative of the level of smoke is wirelessly communicated from the wireless device to an electronic device located remote from the wireless device over the available radio frequency channel.

20. The system for smoke detection of claim 17, further comprising:
means for determining a fault condition of the wireless device; and
means for wirelessly communicating information indicative of the fault condition from the wireless device to an electronic device located remote from the wireless device.

* * * * *

UNITED STATES PATENT AND TRADEMARK OFFICE
CERTIFICATE OF CORRECTION

Page 1 of 1

PATENT NO. : 8,963,726 B2
APPLICATION NO. : 14/165003
DATED : February 24, 2015
INVENTOR(S) : Lawrence Kates It is certified that error appears in the above-identified patent and that said Letters Patent is hereby corrected as shown below:

In the Claims

Column 26, line 6, please replace "2" with --1--.

Signed and Sealed this
Thirtieth Day of June, 2015

Michelle K. Lee
*Director of the United States Patent and Trademark Office*